United States Patent
Scheibel et al.

(12) 
(10) Patent No.: US 6,566,319 B1
(45) Date of Patent: *May 20, 2003

(54) CLEANING PRODUCTS COMPRISING IMPROVED ALKYLARYLSULFONATE SURFACTANTS PREPARED VIA VINYLIDENE OLEFINS AND PROCESSES FOR PREPARATION THEREOF

(75) Inventors: Jeffrey John Scheibel, Loveland, OH (US); Kevin Lee Kott, Loveland, OH (US); Thomas Anthony Cripe, Loveland, OH (US); Daniel Stedman Connor, Cincinnati, OH (US); James Charles Theophile Roger Burckett-St. Laurent, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/478,906

(22) Filed: Jan. 7, 2000

Related U.S. Application Data

(63) Continuation of application No. PCT/IB98/01098, filed on Jul. 20, 1998.
(60) Provisional application No. 60/053,186, filed on Jul. 21, 1997.

(51) Int. Cl.[7] ............................................. C11D 17/00
(52) U.S. Cl. ........................ 510/357; 510/424; 510/426; 510/428
(58) Field of Search ............................... 510/424, 426, 510/428, 357

(56) References Cited

U.S. PATENT DOCUMENTS

| | | | | |
|---|---|---|---|---|
| 2,477,382 A | 7/1949 | Lewis | ........................ | 260/671 |
| 2,564,072 A | 8/1951 | Lien et al. | .................. | 260/671 |
| 3,196,174 A | 7/1965 | Cohen | ........................ | 260/505 |
| 3,238,249 A | 3/1966 | Mirviss et al. | .............. | 260/505 |
| 3,312,745 A | 4/1967 | Habeshaw et al. | .......... | 260/638 |
| 3,341,614 A | 9/1967 | Wirth et al. | ................. | 260/671 |
| 3,351,654 A | 11/1967 | Gudelis | ....................... | 260/505 |
| 3,355,484 A | 11/1967 | Bloch | .......................... | 260/505 |
| 3,427,342 A | 2/1969 | Brooks et al. | .............. | 260/458 |
| 3,442,964 A | 5/1969 | Oldham | ....................... | 260/671 |

(List continued on next page.)

FOREIGN PATENT DOCUMENTS

| | | | | |
|---|---|---|---|---|
| AU | 39394/89 | 2/1990 | ............. | C07C/2/02 |
| CA | 2201953 | 10/1997 | ............. | C07C/5/27 |
| DE | 42 24 947 | 2/1994 | ........... | C11D/3/386 |
| DE | 42 36 698 | 2/1994 | ........... | C11D/3/386 |
| EP | 0 364 012 | 4/1980 | ......... | C07C/303/24 |
| EP | 0 321 177 | 6/1989 | ........... | C01B/33/34 |
| EP | 0 466 558 | 1/1992 | ......... | C07C/15/107 |
| EP | 0 469 940 | 2/1992 | ......... | C07C/15/107 |
| EP | 0 807 616 | 11/1997 | ............. | C07C/2/70 |
| FR | 2697246 | 4/1994 | ......... | C07C/15/107 |
| GB | 936 882 | 9/1963 | | |
| GB | 2 083 490 | 3/1982 | | |

(List continued on next page.)

OTHER PUBLICATIONS

"Petroleum–Based Raw Materials for Anionic Surfactants", Surfactant Science Series, vol. 7, Part 1, Chapter 2, pp. 11–86, Ed. W. M. Linfield, Marcel Dekker, Inc., New York (1996).
Nooi, J. R., et al., "Isomerization Reactions Occurring on Alkylation of Benzene with Some Branched Long–Chain 1–Alkenes", Recueil, vol. 88, No. 4, pp. 398–410 (1969).
Research Disclosure No. 41412, "Hydrocarbon Mixture", Research Disclosure, vol. 414 (Oct. 1998).
U.S. patent application Ser. No. 09/479,369, Jan. 7, 2000, Scheibel et al.
U.S. patent application Ser. No. 09/478,908, Jan. 7, 2000, Scheibel et al.
U.S. patent application Ser. No. 09/479,365, Jan. 7, 2000, Kott et al.
U.S. patent application Ser. No. 09/478,906, Jan. 7, 2000, Scheibel et al.
U.S. patent application Ser. No. 09/479,364, Jan. 7, 2000, Connor et al.

*Primary Examiner*—Necholus Ogden
(74) *Attorney, Agent, or Firm*—Ian S. Robinson; C. Brant Cook; Kim W. Zerby

(57) ABSTRACT

Cleaning compositions, especially laundry detergents and the like, comprising (i) modified alkylarylsulfonate surfactants, e.g., modified alkylbenzenesulfonates, which are the product of particular processes and (ii) cleaning adjuncts such as enzymes and bleaches. Processes for making the cleaning products, including processes comprising vinylidene olefin production, alkylation of arenes, sulfonation and domestic cleaning product formulation. VO production is used to introduce particular limited branching into an alpha-olefinic feedstock which, converted to dimer form, has from about 10 to about 16, preferably from about 12 to about 14 carbon atoms. Preferred processes maximize the amount of vinylidene olefin useful for detergent manufacture, and minimize deep internal olefin production. Further, an alkylation step, preferably having an internal isomer selectivity of from 0 to no more than about 40 is used, in which the VO monoalkylates arenes such as benzene, in presence of an alkylation catalyst preferably comprising an at least partially crystalline, porous zeolite-containing solid, the zeolite being at least partially acidic and having intermediate pore size. Preferred alkylation catalysts include at least partially dealuminized acidic mordenites.

44 Claims, No Drawings

U.S. PATENT DOCUMENTS

| | | | | |
|---|---|---|---|---|
| 3,442,965 A | 5/1969 | Oldham | ......................... | 260/671 |
| 3,491,030 A | 1/1970 | Fields | ........................ | 252/161 |
| 3,492,364 A | 1/1970 | Jones et al. | .................. | 260/671 |
| 3,562,797 A | 2/1971 | Hu | ........................... | 260/683.3 |
| 3,674,885 A | 7/1972 | Griesinger et al. | ......... | 260/671 |
| 4,235,810 A | 11/1980 | Osselet et al. | ............... | 260/505 |
| 4,259,193 A | 3/1981 | Tirtiaux et al. | ................ | 252/33 |
| 4,301,316 A | 11/1981 | Young | ........................ | 585/455 |
| 4,301,317 A | 11/1981 | Young | ........................ | 585/455 |
| 4,409,136 A | * 10/1983 | Cheng | ........................ | 252/540 |
| 4,414,130 A | * 11/1983 | Cheng | ........................ | 252/140 |
| 4,447,664 A | 5/1984 | Murchison et al. | ......... | 585/323 |
| 4,533,651 A | 8/1985 | Masters et al. | ............. | 502/117 |
| 4,587,374 A | 5/1986 | Peters | ........................ | 585/670 |
| 4,645,623 A | 2/1987 | Dolan et al. | ................. | 252/558 |
| 4,731,497 A | 3/1988 | Grey | ........................ | 585/455 |
| 4,855,527 A | 8/1989 | Page et al. | .................. | 585/527 |
| 4,870,038 A | 9/1989 | Page et al. | ..................... | 502/62 |
| 4,959,491 A | 9/1990 | Threlkel | ..................... | 562/94 |
| 4,962,256 A | 10/1990 | Le et al. | ..................... | 585/467 |
| 4,973,788 A | 11/1990 | Lin et al. | .................... | 585/511 |
| 4,990,718 A | 2/1991 | Pelrine | ....................... | 585/455 |
| 4,996,386 A | 2/1991 | Hamilton, Jr. et al. | ...... | 585/646 |
| 5,026,933 A | 6/1991 | Blain et al. | .................... | 585/7 |
| 5,030,785 A | 7/1991 | Huss, Jr. et al. | ............ | 585/456 |
| 5,087,788 A | 2/1992 | Wu | ............................ | 585/512 |
| 5,146,026 A | 9/1992 | Berna et al. | ................ | 585/467 |
| 5,177,280 A | 1/1993 | Juguin et al. | ............... | 585/323 |
| 5,196,574 A | 3/1993 | Kocal | ........................ | 562/94 |
| 5,196,624 A | 3/1993 | Threlkel et al. | ............ | 585/513 |
| 5,196,625 A | 3/1993 | Threlkel et al. | ............ | 585/513 |
| 5,198,595 A | 3/1993 | Lee et al. | .................... | 585/467 |
| 5,210,060 A | 5/1993 | Radlowski et al. | ......... | 502/202 |
| 5,243,116 A | 9/1993 | Lee et al. | .................... | 585/467 |
| 5,245,072 A | 9/1993 | Giancobbe et al. | ........... | 560/99 |
| 5,246,566 A | 9/1993 | Miller | ........................ | 208/27 |
| 5,258,566 A | 11/1993 | Kresge et al. | ............. | 585/467 |
| 5,302,732 A | 4/1994 | Steigleder et al. | ............ | 554/98 |
| 5,326,928 A | 7/1994 | Benazzi et al. | ............. | 585/820 |
| 5,334,793 A | 8/1994 | Kocal | ........................ | 585/323 |
| 5,344,997 A | 9/1994 | Kocal | ........................ | 568/628 |
| 5,401,896 A | 3/1995 | Kuehl et al. | ................ | 585/455 |
| 5,491,271 A | 2/1996 | Marinangeli et al. | ....... | 585/468 |
| 5,510,306 A | 4/1996 | Murray | ....................... | 502/64 |
| 5,602,292 A | 2/1997 | Perego et al. | ............... | 585/750 |
| 5,625,105 A | 4/1997 | Lin et al. | .................... | 585/511 |
| 5,811,612 A | 9/1998 | Girotti et al. | ............... | 585/467 |
| 5,811,623 A | 9/1998 | Ryu et al. | ................... | 585/671 |

FOREIGN PATENT DOCUMENTS

| | | | | |
|---|---|---|---|---|
| GB | 2 278 125 | 11/1994 | ............ | C11D/1/12 |
| RU | 793972 | 1/1981 | ............ | C07C/2/22 |
| WO | WO 88/07030 | 9/1988 | ............ | C07C/2/32 |
| WO | WO 95/17961 | 7/1995 | ............ | B01J/29/06 |
| WO | WO 95/18084 | 7/1995 | ............ | C07C/5/27 |
| WO | WO 95/21225 | 8/1995 | ............ | C09K/7/00 |
| WO | WO 97/01521 | 1/1997 | ............ | C07C/1/04 |
| WO | WO 97/29063 | 8/1997 | ........ | C07C/15/107 |
| WO | WO 97/29064 | 8/1997 | ........ | C07C/15/107 |
| WO | WO 97/47573 | 12/1997 | ............ | C07C/2/66 |

* cited by examiner

CLEANING PRODUCTS COMPRISING IMPROVED ALKYLARYLSULFONATE SURFACTANTS PREPARED VIA VINYLIDENE OLEFINS AND PROCESSES FOR PREPARATION THEREOF

CROSS REFERENCE

This is a continuation under 35 USC §120 of PCT International Application Serial No. PCT/IB98/01098, filed Jul. 20, 1998; which claims priority to Provisional Application Serial No. 60/053,186, filed Jul. 21, 1997.

FIELD OF THE INVENTION

This invention is in the field of cleaning compositions, especially laundry detergents and the like, comprising modified alkylarylsulfonate surfactants, e.g., modified alkylbenzenesulfonates having specific light branching, which are the product of particular processes. The compositions further comprise specified cleaning adjuncts, such as enzymes or bleaches. The invention is also in the field of processes for making cleaning products, including processes comprising vinylidene olefin (VO) production, alkylation of arenes, sulfonation and domestic cleaning product formulation. VO production is used to introduce particular limited branching into an olefinic feedstock, preferably alpha-olefinic feedstock having carbon number consistent with making VO of from about 10 to about 16, preferably from about 10 to about 13 carbon atoms, effectively providing a "delinearized" long-chain olefin. Preferred processes maximize the amount of VO useful for detergent manufacture, and minimize deep internal olefin production. Further, an alkylation step, preferably having an internal isomer selectivity of from 0 to no more than about 40 is used, in which the VO monoalkylates arenes such as benzene, in presence of an alkylation catalyst, preferably comprising an at least partially crystalline, porous zeolite-containing solid, the zeolite being at least partially acidic and having intermediate pore size. Preferred alkylation catalysts include at least partially dealuminized acidic mordenites.

BACKGROUND OF THE INVENTION

Historically, highly branched alkylbenzenesulfonate surfactants, such as those based on tetrapropylene (known as "ABS" or "TPBS") were used in detergents. However, these were found to be very poorly biodegradable. A long period followed of improving manufacturing processes for alkylbenzenesulfonates, making them as linear as practically possible ("LAS"). The overwhelming part of a large art of linear alkylbenzenesulfonate surfactant manufacture is directed to this objective. All relevant large-scale commercial alkylbenzenesulfonate processes in use today are directed to linear alkylbenzenesulfonates. However, linear alkylbenzenesulfonates are not without limitations; for example, they would be more desirable if improved for hard water and/or cold water cleaning properties.

In the petroleum industry, various processes have more recently been developed, for example for producing low viscosity lube oil, which the inventors have now discovered provide new insight on how to delinearize hydrocarbons for detergent manufacture to a limited and controlled extent. Such delinearization, however, is not a feature of any current commercial processes in the different field of alkylbenzenesulfonate surfactant manufacture for consumer products. This is not surprising, in view of the overwhelming volume of LAS surfactant art teaching toward linear compounds and away from delinearization.

The majority of commercial processes for making alkylbenzenes rely on HF or aluminum chloride catalyzed alkylation of benzene. Quite recently, it has been discovered that certain zeolite catalysts can be used for alkylation of benzene with olefins. Such a process step has been described in the context of otherwise conventional processes for manufacture of linear alkylbenzenesulfonates. For example, the DETAL® process of UOP uses a zeolite alkylation catalyst. The DETAL® process and all other current commercial processes for alkylbenzenesulfonate manufacture as currently practiced are well characterized based on the product they produce and all fail to meet the internal isomer selectivity requirements of the preferred inventive process and alkylation catalyst defined hereinafter. Other recent literature describes the use of mordenite as an alkylation catalyst, but no such disclosure makes the combination of specific process steps required by the instant invention. Moreover, in view of the linearity desired in alkylbenzenesulfonate products of conventionally known processes, they also generally include steps directed to the provision or making of a substantially linear hydrocarbon, not a delinearized one, prior to the alkylation. A possible exception is in U.S. Pat. No. 5,026,933 which includes, for example, oligomerization of lower olefin such as propylene under narrowly defined conditions using collidine-deactivated ZSM-23 to form a composition comprising a tetramer assertedly having 1.3 methyl branches per chain, followed by fractionation and an alkylation using mordenite catalyst. See Example XVII. See also U.S. Pat. No. 4,990,718 in the field of lubricant manufacture, in which an alkylbenzene is made for petrochemical industry additive purposes via a process that produces a vinylidene olefin by dimerization in presence of chromium catalyst but in which the vinylidene yield is adversely affected by oligomerization and deep internal olefin production and in which, in fact, the vinylidene dimer is not the major product, requiring removal of major amounts of non-vinylidene olefin prior to alkylation. The processes of '933 and '718 have numerous shortcomings from the standpoint of the detergent industry in terms of cost, catalyst limitations in the propylene oligomerization or olefin dimerization stage, presence of large volumes of distillation fractions that would need to be discarded or find nondetergent customers, and limited range of product compositions, including mixtures of chainlengths attainable. Such developments by the petroleum industry are, in short, not optimal from the standpoint of the expert formulator of detergent products.

Also of interest herein are U.S. Pat. Nos. 5,625,105 and 4,973,788 which relate to recent innovations in the manufacture of vinylidene olefins. These processes do not identify the desirability of arriving at modified alkylbenezenesulfonate surfactants or cleaning products as described herein, nor do they describe how best to accomplish such objectives. The inventors have now found that VO production according to '105 or '788 can be particularly useful as sub-processes in the context of the present invention.

BACKGROUND ART

U.S. Pat. Nos. 5,625,105; 4,973,788; 5,026,933; 4,990,718; 4,301,316; 4,301,317; 4,855,527; 4,870,038; 2,477,382; EP 466,558, Jan. 15, 1992; EP 469,940, Feb. 5, 1992; FR 2,697,246, Apr. 29, 1994; SU 793,972, Jan. 7, 1981; U.S. Pat. Nos. 2,564,072; 3,196,174; 3,238,249; 3,355,484; 3,442,964; 3,492,364; 4,959,491; WO 88/07030, Sep. 25, 1990; U.S. Pat. Nos. 4,962,256, 5,196,624; 5,196,625; EP 364,012 B, Feb. 15, 1990; U.S. Pat. No. 3,312,745; 3,341,614; 3,442,965; 3,674,885; 4,447,664; 4,533,651; 4,587,

374; 4,996,386; 5,210,060; 5,510,306; WO 95/17961, Jul. 6, 1995; WO 95/18084; and U.S. Pat. No. 5,087,788 are useful by way of background to the invention. The manufacture of alkylbenzenesulfonate surfactants has recently been reviewed. See Vol. 56 in "Surfactant Science" series, Marcel Dekker, New York, 1996, including in particular Chapter 2 entitled "Alkylarylsulfonates: History, Manufacture, Analysis and Environmental Properties", pages 39–108 which includes 297 literature references. Documents referenced herein are incorporated in their entirety.

SUMMARY OF THE INVENTION

The present invention is predicated on an unexpected discovery of superior consumer cleaning products such as laundry detergents, dishwashing agents and the like incorporating modified alkylarenesulfonate surfactants, especially modified alkylbenzenesulfonate surfactants which are made by a process which combines a specifically defined delinearization step, involving the manufacture of a vinylidene olefin, with a particularly defined selective alkylation step. The invention also relates to processes for the manufacture of such surfactants and cleaning products.

Accordingly, in one aspect, the present invention relates to a cleaning product comprising: (i) from about 0.1% to about 99% of a modified alkylarylsulfonate surfactant, wherein said modified alkylarylsulfonate surfactant (preferably a modified alkylbenzenesulfonate surfactant) is the product of a process comprising the following steps: (a) a step of reacting, in the presence of a dimerization catalyst, an olefinic feedstock comprising alpha-olefins or mixtures thereof to form one or more vinylidene olefins having a carbon content of from $C_{10}$ to $C_{16}$, preferably from $C_{10}$ to $C_{14}$; (b) a step of alkylating an arene selected from benzene, toluene and mixtures thereof, preferably benzene, with said vinylidene olefin, in the presence of an alkylation catalyst; (c) a step of sulfonating the product of step (b); and, optionally, (d) a step of neutralizing the product of step (c); and (ii) from about 0.00001% to about 99% of cleaning product adjuncts.

A preferred alkylation step in making the modified alkylarylsulfonate surfactant is one having an internal isomer selectivity, as defined hereinafter, of from 0 to no more than about 40, more preferably 20 or lower, more preferably still, 10 or lower. The preferred alkylation catalyst for combining the vinylidene olefin with the aromatic compound comprises a moderate acidity, medium-pore zeolite defined in detail hereinafter. A particularly preferred alkylation catalyst comprises at least partially dealuminized and at least partially acidic mordenites.

In a preferred cleaning product herein, the modified alkylarylsulfonate surfactant is the modified alkylbenzenesulfonate surfactant formed when said arene is benzene; such a composition can comprise: (i) from about 1% to about 40% of said modified alkylarenesulfonate surfactant and (ii) from about 0.01% to about 99% of said cleaning product adjuncts. The "cleaning product adjuncts" are adjuncts suitable for laundry detergents and in this embodiment must comprise at least one member selected from the group consisting of detersive enzymes, oxygen bleaches, bleach activators, bleach catalysts, photobleaches, brighteners, detersive adjunct polymers, surfactants other than said modified alkylarylsulfonate surfactant (for example linear alkylbenzenesulfonate surfactants and other common anionic, nonionic, zwitterionic or cationic surfactants), and mixtures thereof.

The present invention also encompasses a process comprising the following steps in the order indicated: (a) a dimerization step, comprising reacting, in the presence of a dimerization catalyst, an olefinic feedstock comprising alpha-olefins or mixtures thereof to form one or more vinylidene olefins having a carbon content of from $C_{10}$ to $C_{16}$, preferably from $C_{10}$ to $C_{14}$; and (b) an alkylation step having an internal isomer selectivity of from 1 to 40, comprising reacting in the presence of an alkylation catalyst, an arene selected from benzene, toluene and mixtures thereof, more preferably benzene, with said vinylidene olefin; whereby a modified alkylarene is produced, said modified alkylarene being useful as a precursor for alkylarylsulfonate surfactants adapted for use in cleaning products.

Preferred among such process embodiments is a process as described supra wherein said arene is benzene; said process further comprising after step (b), (c) a sulfonation step, comprising reacting the product of step (b) with a sulfonating agent; whereby a modified alkylbenzenesulfonic acid is produced, said modified alkylbenzenesulfonic acid being adapted for use in cleaning products.

Moreover the invention also includes a process further comprising after step (c), (d) a neutralization step, comprising reacting the product of step (c) with an alkali; whereby a modified alkylbenzenesulfonate surfactant is produced, said modified alkylbenzenesulfonate surfactant being adapted for use in cleaning products.

In another variation, the present invention encompasses a process having the steps of making the intermediate modified alkylbenzene or alkyltoluene as described in steps (a) and (b); blending the modified alkylbenzene and/or alkyltoluene with a conventional linear alkylbenzene, for example one made by the DETAL® process, sulfonating the blended alkylbenzenes and/or alkyltoluenes; and one or more steps selected from: neutralizing the sulfonated product of the preceding step; and mixing the same sulfonated product with one or more cleaning product adjunct materials; thereby forming a cleaning product.

Moreover, more generally, the invention encompasses cleaning products including heavy-duty and light-duty laundry detergents, hard surface cleaners, dishwashing detergents, laundry bars, shampoos and the like formed by any of the processes described.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Process Embodiments

As noted in the summary, the present invention relates especially to cleaning compositions comprising certain modified alkylarylsulfonate surfactants, especially modified alkylbenzenesulfonate surfactants, and to processes for preparing such modified alkylbenzenesulfonate surfactants suitable for use in cleaning products such as laundry detergents, hard surface cleaners, dishwashing detergents and the like. The invention also relates to the intermediate alkylbenzenesulfonates and to obvious variants, most notably the corresponding alkyltoluenes and alkyltoluenesulfonate surfactants though naphthalene analogs also have some utility as detergent additives. While most discussion herein refers explicitly to the alkylbenzene derivatives, the readily accessible alkyltoluene and other alkyl alkylaromatic derivatives of lesser commercial importance remain within the spirit and scope of the invention.

In its process embodiments, the present invention includes a process comprising: (a) a dimerization step, comprising reacting, in the presence of a dimerization catalyst (preferably selected from alkylaluminum catalysts and metallocene catalysts, more preferably trialkylaluminum catalysts) an olefinic feedstock comprising alpha-olefins or mixtures thereof to form one or more vinylidene olefins having a carbon content of from $C_{10}$ to $C_{16}$; and (b) an alkylation step having an internal isomer selectivity of from 0 to 40, preferably wherein said internal isomer selectivity of step (b) is no more than about 20, comprising reacting in the presence of an alkylation catalyst, (preferably a shape-selective zeolite-containing alkylation catalysts in at least partially acidic form) an arene selected from benzene, toluene and mixtures thereof, with said vinylidene olefin whereby a modified alkylarene is produced. This modified alkylarene is useful as a precursor for alkylarylsulfonate surfactants adapted for use in cleaning products. In preferred processes, the arene used in the alkylation step, (b), is benzene.

The process of the invention preferably further comprises (c) a sulfonation step, comprising reacting the product of step (b) with a sulfonating agent; whereby a modified alkylbenzenesulfonic acid is produced. This modified alkylbenzenesulfonic acid is especially useful in cleaning products, including, for example, acidic hard surface cleaners. The sulfonic acid form of any of the modified alkylarylsulfonates herein can also be incorporated directly into an alkaline cleaning product such as a laundry detergent, in which neutralization can occur in-situ.

More commonly, the modified alkylbenzenesulfonic acid is neutralized before incorporation into cleaning products. Thus the invention includes a process further comprising: (d) a neutralization step, comprising reacting the product of step (c) with an alkali; whereby a modified alkylbenzenesulfonate surfactant is produced, said modified alkylbenzenesulfonate surfactant being adapted for use in cleaning products.

Modifying an alkylarylsulfonate surfactant by reducing linearity or "delinearization", as effectively provided for in the present process, contradicts most recent developments in alkylbenzenesulfonate detergent manufacture, which are directed to increasing linearity based on the notion (which the inventors believe is incorrect) that only strict linearity will guarantee environmental compatibility. Of the essence in the present invention is the notion that linearity reduction processing by use of vinylidene olefins, especially when combined with a particular type of alkylation later in the process, is not necessarily incompatible with maintaining biodegradability and can at the same time lead to important compositional advantages, in performance or end-result terms, of the modified alkylbenzenesulfonate product and consumer products containing it. This in turn offers advantages such as the ability to reduce the level of, or simplify the formulation of, alkylbenzenesulfonate surfactants in consumer products. Moreover, the modified alkylbenzenesulfonate surfactants produced herein are especially useful in the context of a particular subset of modem detergent adjuncts as described elsewhere herein.

Also encompassed herein is the process wherein a zeolite form of the alkylation catalyst in step (b) is selected from the group consisting of mordenite, ZSM-4, ZSM-12, ZSM-20, offretite, gmelinite and zeolite beta in at least partially acidic form; and the process wherein said internal isomer selectivity in step (b) is from 0 to 10 and wherein said alkylation catalyst in step (b) is substantially in acid form and is contained in a catalyst pellet comprising a conventional binder and further, wherein said catalyst pellet comprises at least about 5% of said alkylation catalyst.

With respect to the selection of alkylation catalyst in the alkylation step (step (b)), the invention includes processes wherein in said step (b), said alkylation catalyst is selected from at least partially acidic mordenite, at least partially acidic, at least partially dealuminized mordenite; and at least partially acidic zeolite beta. Very preferably, the alkylation catalyst in step (b) consists essentially of dealuminized H-mordenite. Also, it is preferred in the instant process to avoid certain catalysts for alkylation. Thus, preferred processes include those wherein aluminum chloride is substantially absent in step (b); and/or wherein HF is substantially absent in step (b); and/or wherein fluoridated zeolites are substantially absent in step (b); and/or wherein sulfuric acid is substantially absent in step (b). More generally, it is preferred that free mineral acids and/or soluble or non-solid Lewis acids such as boron trifluoride are absent in step (b). The term "substantially absent" means at minimum that any quantity of such materials known to be effective for reacting alkenes with benzene will not be deliberately added. More preferably, the amount will be zero.

The opportunity to achieve a meaningful improvement by delinearization or branching in alkylbenzenesulfonate surfactants appears technically to be very limited. This is at least partially on account of the rather restricted range of total carbon content which is necessary for surfactancy in this particular type of surfactant. Most current LAS, to be useful, is based on a range as narrow as from about $C_{10}$ to about $C_{14}$ for the alkyl portion of the alkylbenzenesulfonate molecule. Accordingly, in another process embodiment, the present invention relates to the process as already generally described, wherein $C_{11}$–$C_{14}$ alkyl carbon content of said modified alkylbenzenesulfonate surfactant is increased relative to the alkyl carbon content which would be obtained by indiscriminate reaction of said feedstock olefins having varying chainlengths in said step (a); wherein said increase in $C_{11}$–$C_{14}$ alkyl carbon content is achieved in said step (a) by means of any one of: (I) selecting the feedstock wherein the alpha-olefins consist essentially of a ternary mixture of C5+C6+C7 alpha olefins; (II) selecting the feedstock wherein the alpha-olefins consist essentially of a binary mixture selected from a mixture of $C_5$+$C_7$ alpha-olefins and a mixture of $C_6$+$C_7$ alpha olefins; and (III) selecting the feedstock wherein the alpha-olefins consist essentially of a single alpha-olefin having carbon content of $C_6$ or $C_7$; thereby minimizing formation of vinylidene olefins having carbon content of either less than or equal to $C_{10}$ or of greater than or equal to $C_{15}$. This process embodiment provides for particular control of chainlength which, in combination with the particular alkylation step results in a particularly superior modified alkylarylsulfonate surfactant.

Also of value in the context of the present invention is the process wherein said step (a) is conducted subject to at least one of: I. minimizing oligomerization and/or deep internal olefin production by control of temperature and time; and II. conducting said step or steps without separation or extraction of said vinylidene olefin from oligomers.

In said sulfonation step, (c), of the present process, suitable sulfonating agent is selected from sulfur trioxide, oleum, chlorosulfonic acid, and sulfuric acid. Especially for large-scale production, in said sulfonation step, (c), it is preferred that said sulfonating agent is other than chlorosulfonic acid; for example sulfur trioxide, especially as a sulfur trioxide/air mixture, is preferred. In said neutralization step, (d), alkali is preferably selected from sodium, potassium, ammonium, magnesium and substituted ammonium alkalis and mixtures thereof, more preferably sodium hydroxide, potassium hydroxide, ammonium hydroxide, sodium carbonate, potassium carbonate, and mixtures thereof.

The invention also includes the process further comprising, after step (d), an additional step, (e). of combining the product of step (d) with a cleaning product adjunct; whereby a cleaning product composition is produced.

Stated somewhat differently, but fully consistent with the spirit and scope of the invention, there is further encompassed herein a method for improving a domestic cleaning product containing alkylarylsulfonate surfactant comprising (I) at least one stage of introducing light branching into a linear alkylarene by at least one step of dimerizing an alpha-olefin to form a vinylidene olefin and at least one step of alkylating the vinylidene olefin using an alkylation catalyst having internal isomer selectivity of from 0 to no more than about 40; (II) at least one step of sulfonating the lightly branched modified alkylarene of stage (I); and (III) at least one step of formulating the resulting lightly branched alkylarylsulfonate surfactant, in acid or salt form, and at least one adjunct, into said domestic cleaning product composition.

Further describing the invention will be assisted by providing terminology and more detail of the steps and compositions produced.

Terminology of Olefins

Unless otherwise noted, olefins herein are referred to as follows: Alpha-olefins: R—CH=CH$_2$; such olefins are starting-materials in step (a) for making the modified alkylarylsulfonate surfactants herein and should not be confused with: vinylidene olefins which have the structure

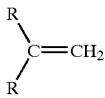

and are prepared by C-1 to C-2 dimerization (vinylidene dimerization) of alpha-olefins. Vinylidene olefins are the principal product of step (a) of the processes herein, and are used as starting-material in the alkylation step (step (b) of the instant process). Also relevant herein, for example as secondary or minor components of feedstocks, are internal olefins, which may be subdivided as:

"di-substituted": R—CH=CH—R;

"tri-substituted":

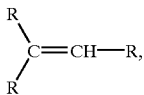

and

"tetra-substituted":

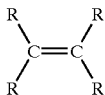

Internal olefins may also be classified as "beta-internal" in which the double bond is connected to a beta-carbon atom as in: R—CH=CH—CH$_3$. The term "deep internal" is used to refer to a di-substituted internal olefin in which the double bond is further towards the center of the olefin as in:

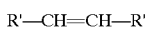

In all the above structures, R represents a hydrocarbon group. In general, any R can vary independently while remaining in conformity with the general structures shown, R' is an aliphatic hydrocarbon group containing at least two carbon atoms. When more than one R' is present in the same molecule or composition, individual to R' can vary independently while remaining in conformity with the general structures shown.

"Beta-internal" olefins referred to are monomeric. This means they contain the same number of carbon atoms as the initial alpha-olefins but the olefinic double bond has moved toward the center of the molecule. "Deep internal" are dimers of initial alpha-olefins, but as is clearly apparent from the structures shown, they are not dimers of the vinylidene type. Dimers in general (whether they be vinylidene olefins or other dimers) contain twice as many carbon atoms as the parent or "initial" olefin, thus, for example, any dimer of 1-hexene contains 12 carbon atoms. "Deep internal" dimers more particularly vary from vinylidene olefins in that their olefinic double bond is in the linear chain near the center of the molecule. In contrast, vinylidene olefin has a double bond that can be considered as being outside the main chain, almost like a "bump" disrupting the linearity of the main chain. If a vinylidene olefin has a chainlength suitable for cleaning surfactant purposes, e.g., C$_{12}$, and the olefinic double bond is reacted without isomerization with one or more moieties including a potentially anionically charged moiety such as a source of sulfonate, then a "two-tailed" surfactant will result. Such a surfactant can optionally be present as an adjunct but is not an essential component in the present invention. If, in contrast, isomerization can occur (which is a function of catalyst systems and other conditions, but particularly dependent on proper selection of certain zeolites such as H-mordenites as used herein) in an otherwise comparable reaction, then a surfactant will be formed which has a single "main chain" containing most of the aliphatic carbon atoms. To this "main chain" will typically be attached a methyl group as a linearity-disrupting "bump". The modified surfactants essential herein all have such linearity-disruption.

It is known in the art that alpha-olefins can be dimerized to form predominantly deep internal olefins using a Friedel-Crafts catalyst such as boron trifluoride. The present invention does not include such Friedel-Crafts dimerizations, at least not in any of its preferred embodiments. Alpha-olefins can also be dimerized to form vinylidene olefins as described in Ziegler U.S. Pat. No. 2,695,327. Aluminum alkyl dimerization, especially as practiced in the older art, can form some amount of deep internal dimers but as disclosed herein can be adapted for the purposes of the present invention with excellent results. The present invention has a strong preference for recently developed process sources of vinylidene olefin, which minimize any byproducts other than the vinylidene olefin.

In terms of understanding the rather different prior arts of, say, petrochemicals such as lube oils and additives in the context of the present invention, it is important to be aware of certain differences in terminology. For example, the term "detergent" or "detergent additive" as used in the petrochemical industry generally usually refers to nonaqueous detergency, as is the case with "detergent" additives added to lube oils or fuels (these can for example be completely lacking the charged groups present in anionic cleaning surfactants, yet be helpful to help unblock fuel injection systems). The term "detergent" is sometimes used in the petrochemical industry with reference to surface-active action in the context of other processes of interest in petrochemicals, such as enhanced oil recovery. In contrast, in the context of the present invention, the terms "detergent"

or "detergent additive" refers to materials which either have cleaning action on textiles, hair or hard surfaces in a consumer product context, or which help such cleaning action, for example by sequestering ions that have an adverse effect on cleaning.

Also in terms of understanding the different prior arts of petrochemicals and cleaning products manufacture, it is helpful to be aware of the great difference in molecular weight focus for useful purposes. For example, in the petrochemical industry, there has been an interest in vinylidene olefins especially from the standpoint of dimerizing or trimerizing to high molecular weights, for example $C_{30}$. In contrast, in cleaning products manufacture, there is a strong preference for aliphatic hydrocarbon feedstocks having from about 10 to about 20 (at most) carbon atoms. In the present inventive context, the aliphatic portion of the modified alkylbenzenes is very preferably not above $C_{18}$, even more preferably not above $C_{14}$, and even more preferably, lies in the range $C_{10}$–$C_{14}$ with highly desired cuts at about $C_{11}$ to $C_{13}$. This difference in molecular weight preference means that what is known in the context of petrochemicals manufacture is not typically reapplied as a straightforward matter to cleaning products manufacture. Moreover, the fact that a particular process step is known in the petrochemical sector does not necessarily mean that it is known or appreciated in the cleaning products sector. Indeed, of many thousands of known petrochemicals processes, comparatively few have been studied or applied in the cleaning products sector. Finally, many processes in the petrochemicals sector may take place on a very large scale as compared with processes in the cleaning products sector. Therefore, the interlocking of processes between the two sectors can be a very difficult matter to accomplish in a practical or economic manner. This is successfully accomplished by the instant invention.

Modified Alkylarenes, Alkylarylsulfonic Acids and Alkylarylsulfonates

The terms "modified alkylbenzenesulfonate", or more generally "modified alkylarylsulfonate" refer to the surfactant product of the processes herein. The term "modified" as applied to the essential surfactants in neutralized form, to the corresponding sulfonic acids, or to their parent alkylarenes especially the modified alkylbenzenes (MAB) formed by steps (a) and (b) of the process herein are all used to indicate that the products of the present process are compositionally different from that of linear alkylbenzenesulfonate surfactants. Preferred compositions produced by the present process are believed to be different from all known commercial alkylbenzenesulfonates, including most particularly, both the so-called "ABS" or "TPBS" or other poorly biodegradable alkylbenzenesulfonates, as well as the so-called "LAS" or linear alkylbenzenesulfonate surfactants. Conventional LAS surfactants are currently commercially available through several processes including those relying on HF-catalyzed or aluminum chloride-catalyzed alkylation of benzene. Other commercial LAS surfactants include LAS made by the DETAL process. The modified alkylbenzenesulfonate surfactants herein are also believed to be compositionally different from those made by alkylating linear olefins using fluoridated zeolite catalyst systems, including fluoridated mordenites. Without being limited by theory, it is believed that the modified alkylbenzenesulfonate surfactants herein have a main aliphatic chain, i.e., they are not surfactants having two approximately equal chains ("two-tailed"). Moreover, the modified alkylbenzenes and alkylbenzenesulfonates herein are believed to be uniquely lightly branched. They typically contain a plurality of isomers and/or homologs. Often, this plurality of species (often tens or even hundreds) is accompanied by a relatively high total content of 2-phenyl isomers, 2-phenyl isomer contents of at the very least 25% and commonly 50% or even 70% or higher being attained. The practitioner should not assume that the structures of the products of the instant process are limited by the precise location of side-chains as suggested by the structure of the vinylidene olefins used to make them. The structures of the instant alkylarylsulfonate derivatives, while not fully known, vary from the expected structure. This is believed to be a consequence of the specific combination of steps, and especially the alkylation step, in the present process. Hence, the present compositions are most fully and unambiguously definable on the basis of a description of how they are made, as done in detail herein. The invention nonetheless also includes any equivalent compositions. Moreover the modified alkylbenzenesulfonate products herein differ in physical properties from known alkylbenzenesulfonate surfactants, for example by having improved surfactant efficiency and low tendency to phase-separate from solution, especially in presence of water hardness.

Vinylidene Olefin Production

Olefin dimerization is used herein to form vinylidene olefin (VO) of the requisite carbon content for useful cleaning product purposes. Carbon contents are given elsewhere herein. The starting alpha-olefinic feedstock or "initial olefin" to be dimerized is a preferably substantially linear alpha-olefin although olefinic feedstocks can vary, for example by including components which are nonreactive under the present conditions and which can be separated by distillation.

It has been discovered that particularly useful individual steps for arriving at the instant cleaning products and now integrated with the specific alkylation step described elsewhere herein can be based on vinylidene olefin production according to U.S. Pat. Nos. 5,625,105 and 4,973,788 incorporated herein by reference. '105 has important advantages in providing vinylidene olefin as a major product in short reaction times that can be exploited by reducing time during which expensive manufacturing equipment is "tied up" for the instant process or can be exploited in terms of generally smaller reactor design for a given throughput. '788 has important advantages especially in terms of providing exceptionally high yields of vinylidene olefin, which can be exploited in the instant process by making it essentially unnecessary to separate the vinylidene olefin from any other product (such as deep internal isomers) before continuing with the alkylation and sulfonation steps.

Also useful herein for vinylidene olefin production are U.S. Pat. Nos. 4,155,946; 4,709,112; 4,795,851; 5,124,465; and 5,516,958. However these other processes have one or more disadvantages compared to '105 and '788. In more detail, vinylidene olefins are branched monoolefins having the structure $(R^1)(R^2)C=CH_2$ conforming with the above-identified general structure but wherein $R^1$ and $R^2$ are more particularly independently variable alkyl groups. Such vinylidene olefins can be produced by dimerizing alpha-olefins. U.S. Pat. No. 4,155,946 discloses a process for dimerizing lower alpha -olefins in which the catalyst system is formed from (1) a trialkylaluminum compound, (2) a salt or complex of nickel, (3) a trivalent phosphorus compound selected from specified groups, and (4) a halogenated phenol.

U.S. Pat. No. 4,709,112 describes a process for dimerizing lower alpha-olefins which uses a catalyst system formed from (1) a trialkylaluminum compound, (2) an organic salt or complex of nickel, (3) a trivalent phosphorus compound selected from specified groups, (4) a fluorinated isopropanol, and (5) a catalyst co-activator selected from specified types of halogenated compounds. This process can also be used herein.

More preferably, U.S. Pat. No. 4,973,788 describes a process for dimerizing a alpha-olefin monomer at a selectivity of at least 85 mole percent. This is accomplished by use of a catalyst which consists essentially of 0.001–0.04 moles of trialkylaluminum per mole of alpha-olefin, and conducting the reaction at a temperature in the range of about 100°–140° C. for a time sufficient to convert at least 80 mole percent of the initial alpha-olefin to a different product. The reaction rate under these conditions is slow, and thus a long reaction time is required. For example it is pointed out that the time required for 90 percent conversion at 120° C. with 0.043 moles of aluminum alkyl catalyst per mole of initial alpha-olefin is about 94 hours, and that with 0.017 moles of the catalyst per mole of initial alpha-olefin the time required at 120° C. is about 192 hours. It is also shown in the patent that although the reaction is faster at 172° C. compared to 120° C., the selectivity to vinylidene dimer is only 71 percent compared to 90 percent with the same catalyst concentration but at 120° C. The '788 process is particularly useful in the context of the present invention.

In terms of mechanism, in the presence of aluminum alkyl, alpha-olefins are dimerized to vinylidene olefins via the Markovnikov route. However a competing reaction which adversely affects yield of vinylidene olefin or the purity thereof is the dimerization to deep internal olefin dimer via the anti-Markovnikov route. Another undesirable competing reaction which normally tends to occur at dimerization temperatures is the isomerization of alpha-olefin to internal isomer olefin via aluminum hydride route or by other known mechanisms. Such internal olefin formation adversely affects the dimer selectivity. It is highly desirable to suppress these competing reactions and be able to achieve high selectivity to vinylidene dimer and without need for multicomponent catalyst systems such as described in U.S. Pat. Nos. 4,155,946 and 4,709,112. This is accomplished in U.S. Pat. Nos. 5,625,105 and 4,973,788, each of which has somewhat different focus, to high speed and high yield respectively, and which are preferred for use in the instant process.

Vinylidene olefin according to U.S. Pat. No. 5,625,105 in More Detail

According to U.S. Pat. No. 5,625,105, vinylidene olefin can be formed with concurrently high yield and short reaction time by dimerizing alpha-olefin with at least one trialkylaluminum compound as the sole catalyst component charged to the reaction vessel. The reactor contains in the range of 0.001 to 0.05 mole of trialkylaluminum per mole of the initial alpha-olefin. Temperature is in the range of over 140° C. and below 172° C. for a period of time in the range of 1 to 24 hours, more typically 6 to 24 hours, sufficient to convert at least 10% (typically much higher, e.g., 60%–80% and above) by weight of the initial alpha-olefin to a different product with at least 80 wt % vinylidene dimer selectivity. The use of these reaction conditions suppresses isomerization to internal olefins and enhances vinylidene dimer selectivity. The U.S. Pat. No. 5,625,105 vinylidene olefin production takes advantage of the exothermic nature of the olefin dimerization reaction. For example, the heat of reaction is about 20 Kcal per g mole of dimer formed. Thus by operating in the above temperature range, external energy requirements and costs can be kept to a minimum. U.S. Pat. No. 5,625,105 has three preferred general modes. One such mode involves use of a single reactor commonly referred to as a "stirred pot reactor" in which the reaction is conducted with agitation on a batch basis. In another such mode the reactor comprises at least two closed vessels in which the reaction is conducted with agitation and continuous feed, the vessels being connected in series such that the feed rate to the first vessel, and the discharge rates from each vessel to the ensuing vessel, where there is an ensuing vessel, are substantially equal to each other. The third mode utilizes a single continuous elongated reactor in which the reaction is conducted with agitation on a continuous basis. When conducting the first or third of these modes it is particularly preferred to perform the reaction such that during at least 50 percent of the time that the reaction mixture is at a temperature above about 110° C.: (a) the vapor space in the reactor is in the range of 0 to 40% (more preferably in the range of up to 30%, still more preferably in the range of no more than 20%, and most preferably in the range of no more than 10%) of the total interior free space of the reactor, and (b) the remainder of the free space in the reactor contains an inert atmosphere. In the case of the second above mode of operation, the reaction is most preferably conducted such that during at least 50% of the time that the reaction mixture is at a temperature above about 110° C. in one or more of the vessels: (a) the vapor space in such vessels is in accordance with the ranges given above, e.g., the total vapor space is in the range of 0 to 40% but most preferably no more than 10% of the total interior free space of the vessels, and (b) the remainder of the free space in the vessels contains an inert atmosphere.

In a preferred embodiment the U.S. Pat. No. 5,625,105 process is conducted whereby the relationship among alpha-olefin conversion, reaction time and catalyst concentration is in accordance with the expression:

$$X = 1 - \exp\{-k[alR]t\}$$

where:

k is a rate constant which is a function of temperature;

[alR] is the molar concentration of aluminum alkyl;

t is reaction time in hours; and

X is alpha-olefin conversion as defined by the expression:

$$1 - [Vi]/[Vi]_0$$

where:

[Vi] is the alpha-olefin molar concentration at time t; and $[Vi]_0$ is the initial alpha-olefin molar concentration.

Values for the rate constant, k, are in terms of liters per gram mole per hour.

The alpha-olefins used in the U.S. Pat. No. 5,625,105 process and as used in preferred embodiments herein can in general be one or more linear alpha-olefins or one or more branched chain alpha-olefins or any mixture of these. All highly preferred embodiments of the instant invention include those wherein the alpha-olefins are linear, or at least wherein non-linear alpha-olefin content is minimized in the alpha-olefinic feedstock. Minor amounts of internal and/or vinylidene monoolefins (e.g., up to 40 mole % of an olefin mixture but preferably less) can be present in the initial alpha-olefin charged to the reactor; though for the purposes of the present invention, a narrower range of alpha-olefin composition is preferred which (a) respects the molecular weight ranges or carbon contents indicated hereinabove which are preferred for ultimately making cleaning product surfactants (modified alkylbenzenesulfonate surfactants) in accordance with the present invention and which (b) do not introduce un-needed internal and/or vinylidene monoolefins. Typical amounts of such internal and/or vinylidene monoolefins are preferably 25 mole % or lower, more preferably still, 10% or lower. The amount of such internal and/or vinylidene olefins, if any, is of course excluded from consideration when calculating the mole ratios of catalyst to initial alpha-olefin used in the process. Typically according to U.S. Pat. No. 5,625,105, the alpha-olefins as used in the process may contain in the range of about 3 to about 30 or more carbon atoms per molecule and preferably the initial alpha-olefin will contain in the range of 4 to 20, and still more preferably in the range of 8 to 16 carbon atoms per molecule. In contrast, for purposes of the instant invention, the initial alpha-olefin will contain in the range of 5 to 8, more preferably 5 to 7, carbon atoms per molecule and the feedstock will be predominantly linear. For some embodiments of the present invention, it is desirable to use a substantially pure single alpha-olefin, such as 1-hexene. In other preferred embodiments, mixtures of alpha-olefins, especially mixtures of 1-pentene and 1-hexene are entirely suitable. In such case, co-dimerization (a special case of dimerization) takes place. Highly preferred combinations of alpha-olefin are described in more detail elsewhere in the specification.

Any aluminum alkyl or "alkylaluminum", preferably trialkylaluminum compound can used as the sole catalytic component "dimerization catalyst" and is charged to a dimerization reaction zone in step (a) in the practice of this invention. In general, the alkyl groups of the alkylaluminum compound will contain from 1 to 30 carbon atoms. However, in the practice of the present invention, a more limited range is highly preferred. Such a range is from 2 to about 18 carbon atoms. Most preferred are trialkylaluminum compounds in which substantially all of the alkyl groups are straight chain primary alkyl groups having in the range of from 2 to about 14 carbon atoms. Especially preferred are triethylaluminum, tributylaluminum, trihexylaluminum, and trioctylaluminum. This is in accordance with the strong preference herein for the production of relatively short-chain, e.g., $C_{10}$–$C_{14}$ vinylidene olefin. Mixtures of aluminum trialkyls can be also used if desired. The hydride content, if any, of the aluminum trialkyl should preferably be quite low, e.g., the aluminum trialkyl should have a maximum aluminum hydride equivalent of not more than about 0.8%. In preferred embodiments the aluminum trialkyl as fed to step (a) of the instant process is essentially hydride-free, i.e., the trialkylaluminum product contains, if any, a maximum of 0.10 wt % of aluminum hydride equivalent, and more preferably a maximum of 0.05 wt % of aluminum hydride equivalent. Without being limited by theory, it is believed that this preference is because the aluminum hydride bond can cause isomerization of 1-olefins to internal olefins.

When using trialkylaluminum compounds as the sole, low-level dimerization catalyst in step (a) of the instant process, it is moreover preferred to conduct the vinylidene olefin making steps of the present process using in the range of about 0.005 to about 0.045 mole of trialkylaluminum per mole of the initial alpha-olefin, and even more preferably about 0.010 to about 0.045 mole of trialkylaluminum per mole of the initial alpha-olefin.

Preferably the dimerization. step (a) is conducted predominantly (more than half of the reaction period) at temperatures in the range of 145° C. to 170° C. and more preferably predominately in the range of 160° C. to 170° C. with reaction periods in the range of 1 to 15 hours (preferably in the range of about 6 to about 15 hours) sufficient to convert at least 80% by weight of the initial alpha-olefin to a different product with at least 80 wt % vinylidene dimer selectivity. A particularly preferred embodiment involves conducting the dimerization predominantly at temperatures in the range of about 165° C.+–3° C. with reaction periods in the range of about 6 to about 12 hours sufficient to convert at least 85% by weight of the initial alpha-olefin to a different product with at least 80 wt % vinylidene dimer selectivity.

Another feature of the U.S. Pat. No. 5,625,105 invention found useful herein is that although Al-H bonds can catalyze isomerization of alpha-olefin to an internal olefin, and although the rate at which trialkylaluminum compounds dissociate into olefin and dialkylaluminum hydride rapidly increases with increasing temperature, the process of this invention enables the formation of vinylidene olefin products of almost as high a purity as the process of U.S. Pat. No. 4,973,788 (also useful herein) but in much shorter reaction periods.

Vinylidene olefin preparation herein (step (a) of the instant process) should be conducted in an environment that is essentially anhydrous and substantially free of oxygen and air. Aluminum trialkyls can react violently with water or compounds containing hydroxyl groups such as alcohols. Thus even a small amount of water, alcohol, or the like, in the system will inactivate some of the aluminum trialkyl. If it known that some water is present in the alpha-olefin, by use of analysis such as Karl Fischer water analysis, the amount of aluminum alkyl dimerization catalyst can be increased to compensate for the water or other active hydrogen component such as alcohol whereby the proper amount of active aluminum trialkyl catalyst remains in the system even after part of the initial aluminum alkyl has been destroyed by the water or other active hydrogen compound. Alternatively, the alpha-olefin feedstock can be pretreated to remove water or alcohol contamination. Likewise the process should be conducted under a dry inert atmosphere e.g., nitrogen, argon, neon, or the like, to prevent catalyst destruction.

In step (a), as in all steps of the instant process, it is desirable to have good mixing in the reactor to ensure uniform temperature. In order to avoid high reactor skin temperature, it is desirable to set the temperature of the reactor heating medium at (or close to) the desired reaction temperature. Both heat from the heating medium and heat of reaction are utilized to bring the reaction mixture from room temperature to the reaction temperature. When the reactor temperature is higher than the temperature of the heating medium, the heat transfer direction will be reversed, i.e., from reaction mixture to the heating medium. Thus, the same heating medium at almost the same temperature may be used both as the heating medium during heat up to reaction temperature, and, as the cooling medium if and when the reaction temperature is passed. Either steam or other heating media such as Dowtherm may be used.

For step (a) of the instant process, at least in an embodiment consistent with the teaching of U.S. Pat. No. 5,625,105, a jacketed 30 gallon glass-lined Pfaudler batch reactor having a heat transfer area to reactor volume ratio of 2.4 $ft^2$:$ft^3$, passage of 110 psig steam through the jacket to control reaction temperature in the range of 165° C.–170° C. is satisfactory.

Precautionary Measures During Making of Vinylidene Dimer

These measures, for the purposes of the instant invention, are as taught in U.S. Pat. No. 5,625,105. Such measures are given in considerable detail not because there is an absolute requirement that each and every such measure should be practiced, but so that the practitioner may select helpful measures which are practically fitting for the present purposes. These measures are especially important when the practitioner wishes to achieve the high yields and use the low catalyst levels as taught in the extensively referenced Amoco patents.

The preferred material of construction at least for the interior of the dimerization reactor is either carbon steel, glass-lining, or mild metals such as copper. Nickel is known to isomers alpha-olefins to internal olefins. Thus, materials which contain Ni such as stainless steel, alloy 20, Inconel, etc., are preferably avoided. Also, Ni-containing feed and transfer lines should be avoided whenever possible. Reactors made with materials such as stainless steel may become passivated after a few cycles of operation to increase dimer yield. Amoco's copending Ser. No. 08/598,801 (Case OL-6962), filed Feb. 5, 1996 by K. F. Lin describes a process in which passivation of ferrous metal surfaces including substantially-nickel free steels and nickel-free steels can be accomplished, and this procedure may be utilized in the practice of this invention. The procedure involves passivation of the surface with air or oxygen. This disclosure is presumably helpful, but is in no way critical to the successful practice of the instant invention. Similar considerations apply to Amoco owned pending application Ser. No. 08/596,812 (Case OL-6963), filed Feb. 5, 1996 by D. H. Krzystowczyk and K. F. Lin, which describes use of acetylenic hydrocarbons for overcoming the devastating effect of nickel on dimer selectivity in a process wherein a alpha-olefin is dimerized by use of an aluminum alkyl catalyst.

Metal impurities in or on surfaces that contact the reactor feed or contents such as Na, Li, etc. may also enhance isomerization of alpha-olefins and should also be avoided wherever possible. Thus there are a number of things that should be done in order to achieve the optimum results achievable by the practice of this invention, especially when using reaction equipment that has been used previously for conducting other kinds of chemical reactions. Such matters are considered below.

Prior to feed transfer to the dimerization reactor used in step (a) of the instant process, the reactor should be cleaned with aqueous and/or organic solvents. The pre-reaction cleanup procedures may include some of the following steps: A) Caustic or acidic wash; B) Water wash; C) Drying (removal of water); D) Heptane (or other heavy paraffin/olefin) wash; and E) Drying (removal of heptane or other heavy paraffin/olefin.) Uppercase letters are used to distinguish these optional steps from the essential steps as described elsewhere herein. Caustic or acidic washing may introduce trace amount of impurities either from the solution or from leaching of material from the interior reactor surfaces. Therefore it is desirable to avoid use of caustic or acidic washing of reactor surfaces. In cases where hot organic solvent wash alone is sufficient to clean up the reactor, aqueous wash is not needed. But in cases where aqueous wash is needed to accomplish the reactor cleanup, use of steam cleaning or hot water wash without use of base or acid is preferred. Caustic or acidic wash should only be used if the other alternatives are inadequate in any given situation. If the reactor history is such that caustic or acidic wash is needed, this should be followed with fresh water washes several times until the quality of final washed water is the same as (or close to) the fresh water used. This may be accomplished by measuring pH or ionic strength (such as Ni, Na, Cl, etc.). Since trace amounts of isomerization promoters can reduce dimer yield tremendously, the purest water available at the plant site (e.g., deionized water or distilled water) is preferably used. After water wash is complete and the final wash water is discharged, the reactor should be blown to dryness with by nitrogen, as any residual water in the reactor will destroy the corresponding amount of aluminum alkyl catalyst. After aqueous wash of the reactor, organic solvent wash (heptane or others) should follow. Hot heptane wash for several hours under agitation conditions can expedite the organic wash process. After heptane wash and discharge of waste heptane, the reactor is preferably purged with nitrogen to dry the reactor. Nitrogen purge with some heat in the reactor accelerates the heptane drying process. If the reaction vessel(s) and/or transfer lines or other auxiliaries that contact the feeds or reaction mixture are composed of nickel-containing steel alloys or other ferrous metal surfaces so that passivation of the contacting surface(s) should be carried out, and if the passivation is to be effected by use of air (or oxygen) rather than by another method such as use of an aliphatic acetylenic hydrocarbon, the cleaned reactor and associated metallic equipment with which the feeds and reaction mixtures come in contact are exposed to air for at least 0.5 hour, preferably for from 0.5 to 3 hours at a temperature of at least about 20° C., such as ambient room temperature up to about 50° C. Shorter exposure periods can be used when employing pure oxygen for surface passivation.

After all of the heptane (or other heavy paraffin/olefin) is removed and the steel surfaces passivated by contact with air or oxygen (if this particular method of passivation has been selected), the dimerization reactor should be maintained with 10 psig $N_2$ at room temperature. All further processing is performed under a blanket of dry inert gas, preferably a nitrogen blanket.

Whenever possible, the feed transfer lines relating to step (a) of the instant invention should be treated with the same diligence as the reactor pretreatment procedure to ensure that no contamination of feeds occurs from the transfer lines.

After the dimerization reactor and associated feed transfer lines have been cleaned up, it is desirable to conduct a blank isomerization operation. This involves charging the reactor under a $N_2$ blanket or purge with alpha-olefin feed of the type to be used for dimerization. In the absence of trialkylaluminum catalyst, the olefin feed is then heated to 165° C. and kept at that temperature for about 12 hours. Such a blank isomerization test makes it possible to determine if there is any isomerization activity in the system in the absence of the trialkylaluminum catalyst. Pilot plant experience has indicated that there is no isomerization in the above glass-lined reactor during the blank isomerization test.

If heavy olefin such as tetradecene is used in the reactor pretreatment, a blank isomerization test can be also carried out with the hot heavy olefin during the reactor cleanup.

The reactor must pass a blank isomerization test before proceeding to dimerization. If it does not, the reactor can be cooked for another 24–48 hours using the same olefin to remove any residual materials which may not be completely removed during the reactor pretreatment. Also, if the reactor or portions of the reaction system that contact the feeds and/or reaction mixture are nickel-containing steel alloys, another passivation treatment at this stage may be necessary or desirable. Then another blank isomerization test should be conducted using another fresh charge of the olefin feed. If this blank isomerization test still fails, further investigation is required to determine the cause. In this connection, failure in a blank isomerization test is deemed to be the formation in the olefin of 0.5% by weight or more of internal olefin as determined by NMR.

After achieving a satisfactory blank isomerization test, the specified amount of trialkylaluminum is charged and mixed with the alpha-olefin in the reactor containing 90 wt % of the specified total amount olefin feed to be used in the reaction. Then the remaining amount of alpha-olefin (10 wt % of specified total olefin feed) is charged to flush out any trialkylaluminum which may be trapped in the feed transfer line.

Although the present invention requires as essential steps only those specifically identified hereinabove, preferred embodiments of the invention can have one or more additional steps at any point based on conventional practice either preceding or following any of the essential steps. Thus step, (a) of the instant process can be expanded into the following sequence of steps which take place prior to use of the product of step (a) in an alkylation step (b). This preferred series of process steps includes: a-i) batch dimerization (the minimum essential step for (a) in the instant process); a-ii) Caustic wash; a-iii) Phase separation; and a-iv) Distillation. The first of these steps is briefly discussed below.

Step (a-i)

Batch dimerization is most preferably carried out at 165° C. using substantially pure linear alpha-olefin (LAO) as the alpha-olefin feed and a charge of triethylaluminum (TEA) or another highly preferred trialkylaluminum as described hereinabove as the catalyst. At a TEA/LAO feed molar ratio of 0.0167, reaction under these conditions typically achieves 90% LAO conversion in 12 hours reaction time. During the dimerization of an alpha-olefin (e.g., 1-octene), TEA will be converted at least in part to trialkylaluminum in which the alkyl groups correspond to the alpha-olefin (in this example, to tri-n-octyl aluminum).

In conducting the dimerization reactions of this invention, it is desirable to have a low volume of vapor space to minimize isomerization in the vapor phase which in turn can reduce selectivity to dimer formation. In general the vapor space or free space in the reactor will fall in the range of 0 to 40%. Preferably, the feed charge is such that at reaction temperature (e.g., 165° C.), the liquid phase occupies at least 70%, more preferably over 80%, still more preferably 90% or more, and most preferably at least about 95% or more, of the internal reactor volume.

The dimerization catalyst can be, and preferably is, recovered from the reaction product and recycled to the dimerization reactor.

Other optional steps surrounding step (a) of the instant process include a-ii) Caustic wash; a-iii) Phase separation; and a-iv) Distillation all as further described in U.S. Pat. No. 5,625,105 incorporated by reference.

Metallocene-containing Vinylidene Dimer Catalyst Systems

Another group of suitable catalyst systems for producing dimers in the form of vinylidene olefins useful herein are catalyst systems comprising a metallocene. A range of suitable catalysts for this step of the instant process, as well as suitable process conditions, are described in U.S. Pat. No. 5,087,788. U.S. Pat. No. 5,087,788 relates to a process for dimerizing an alpha-olefin of the general formula RCH═CH2 where R is alkyl with a carbon number ranging from 1. to about 30, to a vinylidene olefin. Vinylidene olefins are, of course, considered to be sufficiently disrupted from linearity for the purposes of the present invention. Without being limited by theory, this is believed to be a consequence of the selection of a particular alkylation step as described herein. The process of '788 comprises contacting alpha-olefin at temperatures between about −60° C. to about 280° C. with a catalyst for olefin dimerization comprising (a) a metallocene having the general formula (Cp)nMY4-n wherein Cp represents cyclopentadienyl, n is 2 or 3, M is titanium, zirconium or hafnium and each Y is individually selected from hydrogen, $C_1$–$C_5$ alkyl, $C_6$–$C_{20}$ aryl, $C_3$–$C_{20}$ alkoxy, $C_2$–$C_{20}$ ester, and halogen; (b) an alkylaluminoxane other than methylaluminoxane; and (c) trimethylaluminum. More generally, older metallocene-type dimerization catalyst systems such as those of U.S. Pat. No. 4,658,078 can also be useful. The catalysts and procedure such as described by Christoffers and Bergman in J. Amer. Chem. Soc., 1996, 118, 4715–4716 should also be cited as having applicability in the dimerization step of the instant process, especially for smaller scale preparations. In particular, Bergman reports low Al/Zr ratio zirconocene/poly(methylalumoxane) (MAO) catalysts prepared by mixing $Cp_2ZrCl_2$ and MAO in toluene. The Bergman catalyst can also be applied in the context of the teachings of U.S. Pat. No. 5,087,788 for larger-scale purposes. See also in this reference, the listing identified as reference no. 6, which provides a listing of references for several other previously identified catalytic systems for dimerizing alkenes. See U.S. Pat. No. 5,569,642 for more detail on the provision of suitable vinylidene olefin.

Vinylidene olefin manufacture in the instant process preferably avoids use of Friedel-Crafts and/or highly acidic catalyst systems. Chromium catalysts are preferably avoided. All preferred VO manufacturing steps herein produce no $C_{20}$ or higher dimer, preferably no $C_{18}$ dimer and often low or no $C_{16}$ dimer, and have less than about 30% lube yield, preferably less than 10% lube yield, expressed as weight percent as described in U.S. Pat. No. 4,99,718. Thus, the VO manufacturing steps in the present process are clearly not of the kind primarily directed to petroleum additive production or primarily forming typical, higher-molecular weight petroleum additives (see U.S. Pat. No. 4,990,718 for an example of such a process).

Alkylate Production

The invention further includes, after the olefin delinearization/dimerization accomplished in step (a), a monoalkylation step of reacting the delinearized olefin (the vinylidene olefin) with an aromatic hydrocarbon or arene. Preferably the arene is selected from benzene, toluene and mixtures thereof; more preferably it is solely benzene.

Internal Isomer Selectivity and Selection of Alkylation Step

The present processes preferably require an alkylation step (b) having internal isomer selectivity in the range from 0 to 40, preferably from 0 to 20, more preferably still from 0 to 10. The Internal Isomer Selectivity or "IIS" as defined herein is measured for any given alkylation process step by conducting a test alkylation of benzene by 1-dodecene at a molar ratio of 10:1. The alkylation is conducted in the presence of an alkylation catalyst to a conversion of dodecene of at least 90% and formation of monophenyl-dodecanes of at least 60%. Internal isomer selectivity is then determined as:

$$IIS = 100*(1- \text{amount of terminal phenyldodecanes})\text{amount of total phenyldodecanes}$$

wherein amounts are amounts of the products by weight; the amount of terminal phenyldodecanes is the amount of the sum of 2-phenyldodecane and 3-phenyldodecane and the amount of total phenyldodecanes is the amount of the sum of 2-phenyldodecane and 3- phenyldodecane and 4-phenyldodecane and 5-phenyldodecane and 6-phenyldodecane and wherein said amounts are determined by any known analytical technique for alkylbenzene-sulfonates such as gas chromatography. See Analytical Chemistry, November 1983, 55 (13), 2120–2126, Eganhouse et al, "Determination of long-chain alkylbenzenes in environmental samples by argentation thin-layer chromatography—high resolution gas chromatography and gas chromatography/mass spectrometry". In computing IIS according to the above formula, the amounts are divided before subtracting the result from 1 and multiplying by 100. It should of course be understood that the specific alkenes used to characterize or test any given alkylation step for suitability are reference materials permitting a comparison of the alkylation step herein with known alkylation steps as used in making linear alkylbenzenes and permitting the practitioner of the invention to decide if a given known alkylation step is, or is not, useful in the context of the series of process steps constituting the present invention. In the process of the invention as practiced, the hydrocarbon feedstock for alkylation actually used is of course the vinylidene olefin product of step (a) which is specified on the basis of the preceding process steps. Also to be noted, all the current commercial processes for LAS manufacture are excluded from the present invention solely on the basis of the IIS for the alkylation step. For example, LAS processes based on aluminum chloride, HF and the like all have IIS outside of the range specified for the instant process. In contrast, a few alkylation steps described in the literature but not currently applied in commercial alkylbenzenesulfonate production do have suitable IIS and are useful herein.

The better to assist the practitioner in determining IIS and in deciding whether a given alkylation process step is suitable for the purposes of the present invention, the following are more particular examples of IIS determination.

As noted, test alkylation of benzene by 1-dodecene is conducted at a mole ratio of 10:1 benzene to 1-dodecene and the alkylation is conducted in the presence of an alkylation catalyst to a conversion of dodecene of at least 90% and formation of monophenyldodecanes of at least 60%. The alkylation test must in general be conducted in a reaction time of less than 200 hours and at a reaction temperature of from about −15° C to about 500° C., preferably from about 20° C. to 500° C. Pressure and catalyst concentration relative to 1-dodecene can vary widely. No solvent other than benzene is used in the test alkylation. The process conditions used to determine the IIS for the catalyst or alkylation step in question can be based on the literature. The practitioner will use generally appropriate conditions based on a large body of well-documented data for alkylations. For example, appropriate process conditions to determine if an $AlCl_3$ alkylation can be used herein are exemplified by a reaction of 5 mole % $AlCl_3$ relative to 1-dodecene at 20–40° C. for 0.5–1.0 hour in a batch reactor. Such a test demonstrates that an $AlCl_3$ alkylation step is unsuitable for use in the present process. An IIS of about 48 should be obtained. In another example, an appropriate test of alkylation using HF as a catalyst should give an IIS of about 60. Thus, neither $AlCl_3$ alkylation nor HF alkylation is within the scope of this invention. For a medium-pore zeolite such as a dealuminized mordenite, process conditions suitable for determining IIS are exemplified by passing 1-dodecene and benzene at a mole ratio of 10:1 across the mordenite catalyst at a WHSV of 30 $Hr^{-1}$ at a reaction temperature of about 200° C. and a pressure of about 200 psig which should give an IIS of about 0 for the mordenite catalyst. The temperatures and pressures for the exemplary mordenite alkylation test (see also the detailed examples of the instant process hereinafter) are expected to be more generally useful for testing zeolites and other shape-selective alkylation catalysts. Using a catalyst such as H-ZSM-4 one should obtain an IIS of about 18. Clearly both the dealuminized mordenite and H-ZSM-4 catalyzed alkylations give acceptable IIS for the invention, with the mordenite being superior.

Alkylation Catalyst

Accomplishing the required IIS in the alkylation process step is consistent with a tightly controlled selection of alkylation catalysts. Numerous alkylation catalysts are readily determined to be unsuitable. Unsuitable alkylation catalysts include the DETAL® process catalysts, aluminum chloride, HF, HF on zeolites, fluoridated zeolites, non-acidic calcium mordenite (at least when completely non-acidic), and many others. Indeed no alkylation catalyst currently used for alkylation in the commercial production of detergent linear alkylbenzenesulfonates has yet been found suitable.

In contrast, suitable alkylation catalyst herein is selected from shape-selective moderately acidic alkylation catalysts, preferably zeolitic. The zeolite in such catalysts for the alkylation step (step (b)) is preferably selected from the group consisting of mordenite, ZSM-4, ZSM-12, ZSM-20, offretite, gmelinite and zeolite beta in at least partially acidic form. More preferably, the zeolite in step (b) (the alkylation step) is substantially in acid form and is contained in a catalyst pellet comprising a conventional binder and further wherein said catalyst pellet comprises at least about 1%, more preferably at least 5%, more typically from 50% to about 90%, of said zeolite.

More generally, suitable alkylation catalyst is typically at least partially crystalline, more preferably substantially crystalline not including binders or other materials used to form catalyst pellets, aggregates or composites. Moreover the catalyst is typically at least partially acidic. Fully exchanged Ca-form mordenite, for example, is unsuitable whereas H-form mordenite is suitable. This catalyst is useful for the alkylation step identified as step (b) in the claims hereinafter.

The pores characterizing the zeolites useful in the present alkylation process may be substantially circular, such as in cancrinite which has uniform pores of about 6.2 angstroms, or preferably may be somewhat elliptical, such as in mordenite. It should be understood that, in any case, the zeolites used as catalysts in the alkylation step of the present process have a major pore dimension intermediate between that of the large pore zeolites, such as the X and Y zeolites, and the relatively small pore size zeolites ZSM-5 and ZSM-11, and preferably between about 6A and about 7A. Indeed ZSM-5 has been tried and found inoperable in the present invention. The pore size dimensions and crystal structures of certain zeolites are specified in ATLAS OF ZEOLITE STRUCTURE TYPES by W. M. Meier and D. H. Olson, published by the Structure Commission of the International Zeolite Association (1978 and more recent editions) and distributed by Polycrystal Book Service, Pittsburgh, Pa.

The zeolites useful in the alkylation step of the instant process generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain preferred embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

A suitable modifying treatment entails steaming of the zeolite by contact with an atmosphere containing from about 5 to about 100 percent steam at a temperature of from about 250 degree(s) to 1000 degree(s) C. Steaming may last for a period of between about 0.25 and about 100 hours and may be conducted at pressures ranging from sub-atmospheric to several hundred atmospheres.

In practicing the desired alkylation step of the instant process, it may be useful to incorporate the above-described intermediate pore size crystalline zeolites in another material, e.g., a binder or matrix resistant to the temperature and other conditions employed in the process. Such matrix materials include synthetic or naturally occurring substances as well as inorganic materials such as clay, silica, and/or metal oxides. Matrix materials can be in the form of gels including mixtures of silica and metal oxides. The latter may be either naturally occurring or in the form of gels or gelatinous precipitates. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the intermediate pore size zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content ranging from between about I to about 99 percent by weight and more usually in the range of about 5 to about 80 percent by weight of the composite.

A group of zeolites which includes some useful for the alkylation step herein have a silica:alumina ratio of at least 10:1, preferably at least 20:1. The silica:alumina ratios referred to in this specification are the structural or framework ratios, that is, the ratio for the $SiO_4$ to the $AlO_4$ tetrahedra. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite structure are employed. Due care should therefore be taken to ensure that the framework silica:alumina ratio is correctly determined.

Zeolite beta suitable for use herein (but less preferred than H-mordenite) is disclosed in U.S. Pat. No. 3,308,069 to which reference is made for details of this zeolite and its preparation. Such a zeolite in the acid form is also commercially available as Zeocat PB/H from Zeochem.

When the zeolites have been prepared in the presence of organic cations they are catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite; but it does appear to favor the formation of this special type of zeolite. Some natural zeolites may sometimes be converted to zeolites of the desired type by various activation procedures and other treatments such as base exchange, steaming, alumina extraction and calcination. The zeolites preferably have a crystal framework density, in the dry hydrogen form, not substantially below about 1.6 g.cm−3. The dry density for known structures may be calculated from the number of silicon plus aluminum atoms per 1000 cubic Angstroms, as given, e.g., on page 19 of the article on Zeolite Structure by W. M. Meier included in "Proceedings of the Conference on Molecular Sieves, London, April 1967", published by the Society of Chemical Industry, London, 1968. Reference is made to this paper for a discussion of the crystal framework density. A further discussion of crystal framework density, together with values for some typical zeolites, is given in U.S. Pat. No. 4,016,218, to which reference is made. When synthesized in the alkali metal form, the zeolite is conveniently converted to the hydrogen form, generally by intermediate formation of the ammonium form as a result of ammonium ion exchange and calcination of the ammonium form to yield the hydrogen form. It has been found that although the hydrogen form of the zeolite catalyzes the reaction successfully, the zeolite may also be partly in the alkali metal form.

EP 466,558 describes an acidic mordenite type alkylation catalyst also of possible use herein having overall Si/Al atomic ratio of 15–85 (15–60), Na weight content of less than 1000 ppm (preferably less than 250 ppm), having low or zero content of extra-network Al species, and an elementary mesh volume below 2,760 nm3.

U.S. Pat. No. 5,057,472 useful for preparing alkylation catalysts herein relates to concurrent dealumination and ion-exchange of an acid-stable Na ion-containing zeolite, preferably mordenite effected by contact with a 0.5–3 (preferably 1–2.5) M HNO3 solution containing sufficient NH4NO3 to fully exchange the Na ions for NH4 and H ions. The resulting zeolites can have an SiO2:Al2O3 ratio of 15–26 (preferably 17–23):1 and are preferably calcined to at least partially convert the NH4/H form to an H form. Optionally, though not necessarily particularly desirable in the present invention, the catalyst can contain a Group VIII metal (and optionally also an inorganic oxide) together with the calcined zeolite of '472.

Another acidic mordenite catalyst useful for the alkylation step herein is disclosed in U.S. Pat. No. 4,861,935 which relates to a hydrogen form mordenite incorporated with alumina, the composition having a surface area of at least 580 m2/g. Other acidic mordenite catalysts useful for the alkylation step herein include those described in U.S. Pat.

Nos. 5,243,116 and 5,198,595. Yet another alkylation catalyst useful wherein is described in U.S. Pat. No. 5,175,135 which is an acid mordenite zeolite having a silica/alumina molar ratio of at least 50:1, a Symmetry Index of at least 1.0 as determined by X-ray diffraction analysis, and a porosity such that the total pore volume is in the range from about 0.18 cc/g to about 0.45 cc/g and the ratio of the combined meso- and macropore volume to the total pore volume is from about 0.25 to about 0.75.

Particularly preferred alkylation catalysts herein include the acidic mordenite catalysts Zeocat™ FM-8/25H available from Zeochem; CBV 90 A available from Zeolyst International, and LZM-8 available from UOP Chemical Catalysts.

Most generally, any alkylation catalyst may be used herein provided that the alkylation step meets the internal isomer selectivity requirements identified supra.

In general, any alkylation conditions known from the art can be used to alkylate the arene using the vinylidene olefin feedstock herein. Suitable alkylation conditions are further nonlimitingly illustrated in the examples given hereinafter. In general, liquid phase and vapor phase alkylations can be used. Preferred embodiments include liquid-phase alkylations in which essentially only the vinylidene olefin and an excess of arene, especially benzene, are used. The liquid phase alkylations are suitably conducted under pressure, at temperatures above the normal boiling-point of the arene, preferably above 100° C. Temperatures will preferably be maintained below those at which substantial side-reactions occur. The output of the alkylation can be monitored in test runs, suitably using analytical procedures such as those described in connection with IIS or nmr, in order to avoid any excessive temperatures.

Workup Steps

The present invention also encompasses a process according to any of the foregoing aspects or embodiments having the additional steps, of (c) sulfonating the product of step (b); and one or more steps selected from (d) neutralizing the product of step (c); and (e) mixing the product of step (c) or (d) with one or more cleaning product adjunct materials; thereby forming a cleaning product.

Distillation of Modified Alkylbenzenes

Optionally, depending on feedstock and the precise sequence of steps used, the present process can include distillation of modified alkylarenes, (the product of step (b)), for example to remove unreacted starting materials, paraffins, excesses of benzene or other arene (which can be used as reaction solvent for step (b)) and the like. Any conventional distillation apparatus can be used. The general practice is similar to that used for distillation of commercial linear alkylbenzenes (LAB). Suitable distillation steps are described in the hereinabove-referenced Surfactant Science Series review of alkylbenzenesulfonate manufacture.

Sulfonation and Workup

In general, sulfonation of the modified alkylbenzenes in the instant process can be accomplished using any of the well-known sulfonation systems, including those described in the hereinabove-referenced volume "Detergent Manufacture Including Zeolite Builders and Other New Materials" as well as in the hereinabove-referenced Surfactant Science Series review of alkylbenzenesulfonate manufacture. Common sulfonation systems include sulfuric acid, chlorosulfonic acid, oleum, sulfur trioxide and the like. Sulfur trioxide/air is especially preferred. Details of sulfonation using a suitable air/sulfur trioxide mixture are provided in U.S. Pat. No. 3,427,342, Chemithon.

Any convenient workup steps may be used in the present process. Common practice is to neutralize after sulfonation with any suitable alkali. Thus the neutralization step can be conducted using alkali selected from sodium, potassium, ammonium, magnesium and substituted ammonium alkalis and mixtures thereof. Potassium can assist solubility, magnesium can promote soft water performance and substituted ammonium can be helpful for formulating specialty variations of the instant surfactants. The invention encompasses any of these derivative forms of the modified alkylbenzenesulfonate surfactants as produced by the present process and their use in consumer product compositions.

Alternately the acid form of the present surfactants can be added directly to acidic cleaning products, or can be mixed with cleaning ingredients and then neutralized.

Cleaning Products

The present invention encompasses specific cleaning product embodiments. Thus, the invention relates to a cleaning product, especially a domestic cleaning product such as a laundry detergent, dishwashing product or the like, comprising: (i) from about 0.1% to about 99% of a modified alkylarylsulfonate surfactant, wherein said modified alkylarylsulfonate surfactant is the product of the process described in detail elsewhere herein. Such a process can comprise the following steps: (a) a step of reacting, in the presence of a dimerization catalyst, an olefinic feedstock comprising alpha-olefins or mixtures thereof (suitably $C_5$–$C_8$ alpha-olefin or mixtures thereof, more preferably a $C_5$–$C_7$ alpha-olefin or mixtures thereof) to form one or more vinylidene olefins having a carbon content of from $C_{10}$ to $C_{16}$, preferably from $C_{10}$ to $C_{14}$; (b) a step of alkylating an arene selected from benzene, toluene and mixtures thereof, preferably benzene, with said vinylidene olefin, in the presence of an alkylation catalyst; (c) a step of sulfonating the product of step (b); and, optionally, (d) a step of neutralizing the product of step (c); and (ii) from about 0.00001% to about 99% of cleaning product adjuncts.

It should be apparent from the process discussion hereinabove that many, if not all of the preferred cleaning product embodiments of this invention are best described with reference to the process variations that account for their formation. These process limitations should be taken as part of the cleaning product definition in the passages which follow.

Thus, a preferred alkylation step in making the modified alkylarylsulfonate surfactant, and thereby, the cleaning composition of the invention, is one having an internal isomer selectivity of from 0 to no more than about 40, more preferably 20 or lower, more preferably still, 10 or lower. A preferred alkylation catalyst for combining the vinylidene olefin with the aromatic compound, and compatible with achieving the internal isomer selectivity, comprises a moderate acidity, medium-pore zeolite as extensively defined and illustrated in the discussion of alkylation and elsewhere herein. A particularly preferred alkylation catalyst comprises at least partially dealuminized and at least partially acidic mordenites.

A preferred cleaning product herein is one wherein said modified alkylarylsulfonate surfactant is the modified alkylbenzenesulfonate surfactant formed when said arene is benzene; and wherein said cleaning product composition comprises: (i) from about 1% to about 40% of said modified alkylarenesulfonate surfactant and (ii) from about 0.01% to about 99% of said cleaning product adjuncts; and wherein said cleaning product adjuncts are adjuncts suitable for laundry detergents and preferably comprise at least one member selected from the group consisting of detersive enzymes, oxygen bleaches, bleach activators, bleach catalysts, photobleaches, brighteners, detersive adjunct polymers, surfactants other than said modified alkylarylsulfonate surfactant, and mixtures thereof. All such adjuncts can be used at any of the levels disclosed in numerous patents referenced herein. Enzymes, bleach catalysts, photobleaches and several other adjuncts can be used at levels ranging from a few ppm to less than 1%. Other adjuncts, such as builders and surfactants, can be used at typical levels ranging from about 1% to about 30%. Intermediate levels, from about 0.1% to about 10%, are often used with materials such as adjunct polymers. Detersive adjunct polymers more specifically include all polymers known for use in detergents, especially the water-soluble anionic types often used as special-purpose builders and/or antiredeposition agents. Other especially useful polymers are the soil release polymers, especially those based on a substituted terephthalate as described in more detail hereinafter. Other highly preferred polymers include the polyethyleneimines. The practitioner is particularly referred to numerous commonly assigned patents to Procter & Gamble in the field of laundry detergents and cleaning products for more detailed disclosure of such materials and their levels.

Cleaning products herein also include those wherein the C11–C14 alkyl carbon content of said modified alkylbenzenesulfonate surfactant is increased relative to the alkyl carbon content which would be obtained by indiscriminate reaction of said feedstock olefins having varying chain-lengths in said step (a); and wherein said increase in $C_{11}$–$C_{14}$ alkyl carbon content is achieved in step (a) by means of any one of: (I) selecting the feedstock wherein the alpha-olefins consist essentially of a ternary mixture of C5+C6+C7 alpha olefins; (II) selecting the feedstock wherein the alpha-olefins consist essentially of a binary mixture selected from a mixture of C5+C7 alpha-olefins and a mixture of C6+C7 alpha olefins; and (III) selecting the feedstock wherein the alpha-olefins consist essentially of a single alpha-olefin having carbon content of $C_6$ or $C_7$; thereby minimizing formation of vinylidene olefins having carbon content of either less than or equal to $C_{10}$ or of greater than or equal to $C_{15}$.

Cleaning products herein, especially those having the form of heavy-duty laundry detergents, include those wherein the cleaning product adjuncts further comprise a builder other than a polymeric builder. Such a builder can, for example, be a zeolite builder, more particularly, one selected from the group consisting of zeolite A, zeolite P, zeolite maximum aluminum P and mixtures thereof. High-quality Zeolite A in the sodium form and having particle size of from about 0.1 to about 10 micron is especially preferred.

Cleaning products herein also include embodiments wherein said cleaning product adjuncts comprise at least one detersive enzyme selected from the group consisting of proteases, amylases, lipases, cellulases, keratinases, endoglucanases, and mixtures thereof. In one such embodiment, the detersive enzyme is a protease or a combination thereof with other detersive enzymes. In another such embodiment, the detersive enzyme comprises at least one of said detersive enzymes other than protease.

The invention importantly can include combinations of unmodified and modified alkylarylsulfonate surfactants. Thus, a cleaning product is encompassed wherein said surfactant other than said modified alkylarylsulfonate surfactant comprises a linear alkylbenzenesulfonate surfactant; or wherein prior to sulfonation step (c), the product of alkylation step (b) is blended with a linear alkylbenzene; or wherein prior to or concurrent with neutralization step (d), the product of sulfonation step (c) is blended with a linear alkylbenzenesulfonic acid. These very different approaches offer flexibility to the formulator in terms of how to include both linear and modified surfactants in the present compositions, and can have other important advantages, for example in the handling characteristics of intermediates used to form the final cleaning product compositions. Modified alkylbenzenesulfonate surfactant and said linear alkylbenzenesulfonate surfactant can be present at varying ratios, for example they may be incorporated into the cleaning product at a ratio of from 1:100 to 100:1.

Cleaning products herein also include embodiments wherein said modified alkylbenzenesulfonate surfactant is the product of the process wherein said step (a) of reacting said feedstock to form said vinylidene olefin is followed by an additional step, prior to said step (b), of separating vinylidene olefin from deep internal olefins and/or oligomers. suitable for lubricant oil manufacture. Other useful cleaning products are those wherein said modified alkylbenzenesulfonate surfactant is the product of the process wherein said step (a) of reacting said alpha-olefin to form said vinylidene olefin comprises dimerizing, in presence of a dimerization catalyst, a substantially linear alpha-olefin having about half the molecular weight required to form a C10–C14 vinylidene olefin, thereby forming a vinylidene olefin under high-yield conditions not requiring separation of the vinylidene olefin from oligomers or deep internal isomers. Further, based on the processing insights applied herein, the invention includes a cleaning product wherein said dimerization catalyst in step (a) is an aluminum alkyl and wherein step (a) comprises dimerizing said alpha-olefin at a temperature of 165° C.±3° C. with a reaction period in the range of from about 6 hours to about 12 hours sufficient to convert at least 85% by weight of said alpha-olefin to a vinylidene olefin-rich product with at least 80 wt % vinylidene dimer selectivity. Likewise encompassed is a cleaning product wherein said dimerization catalyst in step (a) is an aluminum alkyl and wherein step (a) comprises dimerizing said alpha-olefin using from 0.001–0.04 moles of said catalyst per mole of said alpha-olefin at a temperature in the range of about 100° C. to about 140° C. for a time sufficient to convert at least 80 mole percent of the initial alpha-olefin to a vinylidene olefin-rich product with at least 80 wt % vinylidene dimer selectivity.

Another valuable cleaning product is one wherein said dimerization catalyst in said step (a) is an aluminum alkyl and wherein step (a) comprises dimerizing said alpha-olefin using from 0.001–0.04 moles of said catalyst per mole of said alpha-olefin; and further wherein said step (a) is conducted using measures to limit reactor wall reactions and/or loss of catalyst. More generally, cleaning products are encompassed wherein in said step (a), oligomerization and/or deep internal olefin production are minimized by control of reaction temperature and time; and those wherein the vinylidene olefin containing product of said step (a) is reacted in step (b) without prior separation or extraction of oligomeric byproducts. Preferred cleaning products are those wherein said dimerization catalyst in said step (a) is selected from alkylaluminum catalysts and metallocene catalysts, more preferably trialkylaluminum catalysts such as tri-n-hexylaluminum. In general, the cleaning product adjuncts as used herein are those particular for laundry detergents, dishwashing products and the like. Such adjuncts differ from those commonly used in lube oil additives and/or enhanced oil recovery and are described in detail in this specification.

Cleaning Product Adjunct Materials

Adjunct materials can vary widely and accordingly can be used at widely ranging levels. For example, detersive enzymes such as proteases, amylases, cellulases, lipases and the like as well as bleach catalysts including the macrocyclic types having manganese or similar transition metals all useful in laundry and cleaning products can be used herein at very low, or less commonly, higher levels.

Other cleaning product adjunct materials suitable herein include bleaches, especially the oxygen bleach types including activated and catalyzed forms with such bleach activators as nonanoyloxybenzenesulfonate and/or tetraacetylethylenediamine and/or any of its derivatives or derivatives of phthaloylimidoperoxycaproic acid or other imido- or amido-substituted bleach activators including the lactam types, or more generally any mixture of hydrophilic and/or hydrophobic bleach activators (especially acyl derivatives including those of the $C_6$–$C_{16}$ substituted oxybenzenesulfonates); preformed peracids related to or based on any of the hereinbefore mentioned bleach activators, builders including the insoluble types such as zeolites including zeolites A, P and the so-called maximum aluminum P as well as the soluble types such as the phosphates and polyphosphates, any of the hydrous, water-soluble or water-insoluble silicates, 2,2'-oxydisuccinates, tartrate succinates, glycolates, NTA and many other ethercarboxylates or citrates, chelants including EDTA, S,S'-EDDS, DTPA and phosphonates, water-soluble polymers, copolymers and terpolymers, soil release polymers, cosurfactants including any of the known anionic, cationic, nonionic or zwitterionic types, optical brighteners, processing aids such as crisping agents and/fillers, solvents, antiredeposition agents, silicone/silica and other suds suppressors, hydrotropes, perfumes or pro-perfumes, dyes, photobleaches, thickeners, simple salts and alkalis such as those based on sodium or potassium including the hydroxides, carbonates, bicarbonates and sulfates and the like. When combined with the modified alkylbenzenesulfonate surfactants of the instant process, any of the anhydrous, hydrous, water-based or solvent-borne cleaning products are readily accessible as granules, tablets, powders, flakes, gels, extrudates, pouched or encapsulated forms or the like. Accordingly the present invention also includes the various cleaning products made possible or formed by any of the processes described. These may be used in discrete dosage forms, used by hand or by machine, or may be continuously dosed into all suitable cleaning appliances or delivery devices.

Cleaning Products in Detail

References cited herein are incorporated by reference. The surfactant compositions prepared by the processes of the present invention can be used in encompasses a wide range of consumer cleaning product compositions including powders, granules, gels, pastes, tablets, pouches, bars, types delivered in dual-compartment containers, spray or foam detergents and other homogeneous or multiphasic consumer cleaning product forms. They can be used or applied by hand and/or can be applied in unitary or freely alterable dosage, or by automatic dispensing means, or are useful in appliances such as washing-machines or dishwashers or can be used in institutional cleaning contexts, including for example, for personal cleansing in public facilities, for bottle washing, for surgical instrument cleaning or for cleaning electronic components. They can have a wide range of pH, for example from about 2 to about 12 or higher, and they can have a wide range of alkalinity reserve which can include very high alkalinity reserves as in uses such as drain unblocking in which tens of grams of NaOH equivalent can be present per 100 grams of formulation, ranging through the 1–10 grams of NaOH equivalent and the mild or low-alkalinity ranges of liquid hand cleaners, down to the acid side such as in acidic hard-surface cleaners. Both high-foaming and low-foaming detergent types are encompassed.

Consumer product cleaning compositions are described in the "Surfactant Science Series", Marcel Dekker, New York, Volumes 1–67 and higher. Liquid compositions in particular are described in detail in the Volume 67, "Liquid Detergents", Ed. Kuo-Yann Lai, 1997, ISBN 0-8247-9391-9 incorporated herein by reference. More classical formulations, especially granular types, are described in "Detergent Manufacture including Zeolite Builders and Other New Materials", Ed. M. Sittig, Noyes Data Corporation, 1979 incorporated by reference. See also Kirk Othmer's Encyclopedia of Chemical Technology.

Consumer product cleaning compositions herein nonlimitingly include:

Light Duty Liquid Detergents (LDL): these compositions include LDL compositions having surfactancy improving magnesium ions (see for example WO 97/00930 A; GB 2,292,562 A; U.S. Pat. Nos. 5,376,310; 5,269,974; 5,230,823; 4,923,635; 4,681,704; 4,316,824; 4,133,779) and/or organic diamines and/or various foam stabilizers and/or foam boosters such as amine oxides (see for example U.S. Pat. No. 4,133,779) and/or skin feel modifiers of surfactant, emollient and/or enzymatic types including proteases; and/or antimicrobial agents; more comprehensive patent listings are given in Surfactant Science Series, Vol. 67, pages 240–248.

Heavy Duty Liquid Detergents (HDL): these compositions include both the so-called "structured" or multi-phase (see for example U.S. Pat. Nos. 4,452,717; 4,526,709; 4,530,780; 4,618,446; 4,793,943; 4,659,497; 4,871,467; 4,891,147; 5,006,273; 5,021,195; 5,147,576; 5,160,655) and "non-structured" or isotropic liquid types and can in general be aqueous or nonaqueous (see, for example EP 738,778 A; WO 97/00937 A; WO 97/00936 A; EP 752,466 A; DE 19623623 A; WO 96/10073 A; WO 96/10072 A; U.S. Pat. Nos. 4,647,393; 4,648,983; 4,655,954; 4,661,280; EP 225,654; U.S. Pat. Nos. 4,690,771; 4,744,916; 4,753,750; 4,950,424; 5,004,556; 5,102,574; WO 94/23009; and can be with bleach (see for example U.S. Pat. Nos. 4,470,919; 5,250,212; EP 564,250; U.S. Pat. Nos. 5,264,143; 5,275,753; 5,288,746; WO 94/11483; EP 598,170; EP 598,973; EP 619,368; U.S. Pat. Nos. 5,431,848; 5,445,756) and/or enzymes (see for example U.S. Pat. Nos. 3,944,470; 4,111,855; 4,261,868; 4,287,082; 4,305,837; 4,404,115; 4,462,922; 4,529,5225; 4,537,706; 4,537,707; 4,670,179; 4,842,758; 4,900,475; 4,908,150; 5,082,585; 5,156,773; WO 92/19709; EP 583,534; EP 583,535; EP 583,536; WO 94/04542; U.S. Pat. No. 5,269,960; EP 633,311; U.S. Pat. Nos. 5,422,030; 5,431,842; 5,442,100) or without bleach and/or enzymes. Other patents relating to heavy-duty liquid detergents are tabulated or listed in Surfactant Science Series, Vol. 67, pages 309–324.

Heavy Duty Granular Detergents (HDG): these compositions include both the so-called "compact" or agglomerated or otherwise non-spray-dried, as well as the so-called "fluffy" or spray-dried types. Included are both phosphated and nonphosphated types. Such detergents can include the more common anionic-surfactant based types or can be the so-called "high-nonionic surfactant" types in which commonly the nonionic surfactant is held in or on an absorbent such as zeolites or other porous inorganic salts. Manufacture of HDG's is, for example, disclosed in EP 753,571 A; WO 96/38531 A; U.S. Pat. Nos. 5,576,285; 5,573,697; WO 96/34082 A; U.S. Pat. No. 5,569,645; EP 739,977 A; U.S. Pat. No. 5,565,422; EP 737,739 A; WO 96/27655 A; U.S. Pat. No. 5,554,587; WO 96/25482 A; WO 96/23048 A; WO 96/22352 A; EP 709,449 A; WO 96/09370 A; U.S. Pat. Nos. 5,496,487; 5,489,392 and EP 694,608 A.

"Softergents" (STW): these compositions include the various granular or liquid (see for example EP 753,569 A; U.S. Pat. Nos. 4,140,641; 4,639,321; 4,751,008; EP 315, 126; U.S. Pat. Nos. 4,844,821; 4,844,824; 4,873,001; 4,911, 852; 5,017,296; EP 422,787) softening-through-the wash types of product and in general can have organic (e.g., quaternary) or inorganic (e.g., clay) softeners.

Hard Surface Cleaners (HSC): these compositions include all-purpose cleaners such as cream cleansers and liquid all-purpose cleaners; spray all-purpose cleaners including glass and tile cleaners and bleach spray cleaners; and bathroom cleaners including mildew-removing, bleach-containing, antimicrobial, acidic, neutral and basic types. See, for example EP 743,280 A; EP 743,279 A. Acidic cleaners include those of WO 96/34938 A.

Bar Soaps and/or Laundry Bars (BS&HW): these compositions include personal cleansing bars as well as so-called laundry bars (see, for example WO 96/35772 A); including both the syndet and soap-based types and types with softener (see U.S. Pat. No. 5,500,137 or WO 96/01889 A); such compositions can include those made by common soap-making techniques such as plodding and/or more unconventional techniques such as casting, absorption of surfactant into a porous support, or the like. Other bar soaps (see for example BR 9502668; WO 96/04361 A; WO 96/04360 A; U.S. Pat. No. 5,540,852) are also included. Other handwash detergents include those such as are described in GB 2,292, 155 A and WO 96/01306 A.

Shampoos and Conditioners (S&C): (see, for example WO 96/37594 A; WO 96/17917 A; WO 96/17590 A; WO 96/17591 A). Such compositions in general include both simple shampoos and the so-called "two-in-one" or "with conditioner" types.

Liquid Soaps (LS): these compositions include both the so-called "antibacterial" and conventional types, as well as those with or without skin conditioners and include types suitable for use in pump dispensers, and by other means such as wall-held devices used institutionally.

Special Purpose Cleaners (SPC): including home dry cleaning systems (see for example WO 96/30583 A; WO 96/30472 A; WO 96/30471 A; U.S. Pat. No. 5,547,476; WO 96/37652 A); bleach pretreatment products for laundry (see EP 751,210 A); fabric care pretreatment products (see for example EP 752,469 A); liquid fine fabric detergent types, especially the high-foaming variety; rinse-aids for dishwashing; liquid bleaches including both chlorine type and oxygen bleach type, and disinfecting agents, mouthwashes, denture cleaners (see, for example WO 96/19563 A; WO 96/19562 A), car or carpet cleaners or shampoos (see, for example EP 751,213 A; WO 96/15308 A), hair rinses, shower gels, foam baths and personal care cleaners (see, for example WO 96/37595 A; WO 96/37592 A; WO 96/37591 A; WO 96/37589 A; WO 96/37588 A; GB 2,297,975 A; GB 2,297,762 A; GB 2,297,761 A; WO 96/17916 A; WO 96/12468 A) and metal cleaners; as well as cleaning auxiliaries such as bleach additives and "stain-stick" or other pre-treat types including special foam type cleaners (see, for example EP 753,560 A; EP 753,559 A; EP 753,558 A; EP 753,557 A; EP 753,556 A) and anti-sunfade treatments (see WO 96/03486 A; WO 96/03481 A; WO 96/03369 A) are also encompassed. Detergents with enduring perfume (see for example U.S. Pat. No. 5,500,154; WO 96/02490) are increasingly popular.

Process Integration

The present process can be integrated with current LAB manufacturing processes in any convenient manner. For example, conventional erected plant can be switched to produce the modified alkylbenzenes in their entirety. Alternately, depending on volumes desired or feedstocks available, for example as effluents from the LAB process or based on proximity of feedstock sources from the petrochemical industry, plant for the manufacture of the instant modified alkylbenzenes may be erected as an add-on or complement to an existing LAB facility, or as a stand-alone. Both batch and continuous operation of the present process are envisaged.

In one add-on mode, the present invention encompasses steps of making vinylidene olefin and from the vinylidene olefin, modified alkylbenzene or alkyltoluene using the steps described in detail hereinabove. The modified alkylbenzene or alkyltoluene is blended at a ratio of from about 1:100 to 100: 1, more typically from about 1:10 to about 10:1, for example about 1:5, into a conventional linear alkylbenzene, for example a C11.8 average alkylbenzene or any alkylbenzene produced by the DETAL® process. The blend is then sulfonated, neutralized and incorporated into consumer cleaning product compositions.

The present invention should not be considered limited by the specifics of its illustration in the specification including the examples given for illustration hereinafter. Most generally, the present invention should be taken to encompass any consumer cleaning composition comprising any surfactant product of any type wherein the hydrophobe of the surfactant has been modified by an approach using the essential teachings of the instant process. The present teachings, especially with respect to the delinearization approach, are believed to be reapplicable, for example, to the manufacture of modified alkyl sulfates and other surfactants.

EXAMPLE 1

Modified Alkylbenzenesulfonate Surfactant Prepared via Vinylidene Olefin

Step (a): Providing Vinylidene Olefin 1-hexene is dimerized using tri-n-hexylaluminum as the catalyst. The reaction is performed pursuant to the teachings of U.S. Pat. No. 5,625,105 given in detail hereinabove using a dimerization temperature of 165° C. and a short reaction period of 5 hours. The results are summarized in Table 1. Catalyst concentration is expressed in terms of moles of tri-n-hexylaluminum ("TNHA") per mole of initial 1-hexene. The yield value given in Table 1 for deep internal dimer also includes small amounts of deep internal monomer.

TABLE 1

| Example | TNHA Conc. (moles per mole of initial olefin) | Time, hrs. | Temp. ° C. | Beta-Internal Monomer, wt % | Deep Int.Dimer, wt % | Vinyl-i-dene Dimer, wt % |
|---|---|---|---|---|---|---|
| High speed run | 0.043 | 5 | 165 | 7 | 10 | 83 |

In more detail, 1-hexene is dimerized at 165° C. by charging it with tri-n-hexylaluminum (0.043 moles per mole of 1-hexene) in a stirred 30-gallon glass-lined Pfaudler reactor. The reactor is heated at autogenous pressure maintaining said reaction temperature. Reaction time is 5 hours. The reaction is killed with a caustic wash. Unreacted 1-hexenes and trace water remaining from the wash are removed by stripping at reduced pressure.

Step (b): Alkylating the Product of Step (a) Using an Aromatic Hydrocarbon

To a glass autoclave liner is added 1 mole equivalent of the vinylidene olefin produced in step (a), 10 mole equivalents of benzene and 20 wt. % based on the olefin mixture of a shape selective zeolite catalyst (acidic mordenite catalyst Zeocat™ FM-8/25H). The glass liner is sealed inside a stainless steel rocking autoclave. The autoclave is purged twice with 250 psig $N_2$, and then charged to 1000 psig $N_2$. With mixing, the mixture is heated to 170–190° C. for 14–15 hours at which time it is then cooled and removed from the autoclave. The reaction mixture is filtered to remove catalyst and is concentrated by evaporation of benzene using a rotary evaporator to obtain a clear near-colorless liquid product. The product formed is the desired modified alkylbenzene mixture.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 2

Modified Alkylbenzenesulfonate Surfactant Prepared via Vinylidene Olefin Mixture Step (a): Providing Vinylidene Olefin 1-hexene is dimerized using tri-n-hexylaluminum as the catalyst. The reactions are performed pursuant to the teachings of U.S. Pat. No. 4,973,788 using a dimerization temperature of 120° C. and a long reaction period of 180 hours. The results are summarized in Table 2. Catalyst concentration is expressed in terms of moles of tri-n-hexylaluminum ("TNHA") per mole of initial 1-hexene. The values given for deep internal dimer also include small amounts of deep internal monomer.

TABLE 2

| Example | TNHA Conc. (moles per mole of initial olefin) | Time, hrs. | Temp. ° C. | Beta-Internal Monomer, wt % | Deep Int. Dimer, wt % | Vinylidene Dimer, wt % |
|---|---|---|---|---|---|---|
| Low temp.run | 0.017 | 180 | 120 | 2 | 6 | 92 |

In more detail, 1-hexene is dimerized at 120° C. by charging it with trihexylaluminum (0.017 moles per mole of 1-hexene) in a suitable pressure reactor. Reaction time is about 180 hours. The reaction is killed with a caustic wash. A mixture of 1-pentene and 1-heptene (1:1 by weight) are dimerized using a procedure analogous to that applied to 1-hexene supra. The products of 1-pentene/1-heptene dimerization are blended with the product of 1-hexene dimerization at a weight ratio of 1:2. The high-purity vinylidene olefin mixture is used in further steps of the process after stripping unreacted lower olefins but without distillate removal of beta-internal monomer or deep internal dimer.

Step (b): Alkylating the Product of Step (a) Using an Aromatic Hydrocarbon

To a glass autoclave liner is added 1 mole equivalent of the vinylidene olefin mixture produced in step (a), 20 mole equivalents of benzene and 20 wt. % based on the olefin mixture of a shape selective zeolite catalyst (acidic mordenite catalyst Zeocat™ FM-8/25H). The glass liner is sealed inside a stainless steel rocking autoclave. The autoclave is purged twice with 250 psig $N_2$, and then charged to 1000 psig $N_2$. With mixing, the mixture is heated to 170–190° C. for 14–15 hours at which time it is then cooled and removed from the autoclave. The reaction mixture is filtered to remove catalyst and is concentrated by evaporation of benzene using a rotary evaporator to obtain a clear near-colorless liquid product. The product formed is the desired modified alkylbenzene mixture.

Step (c): Sulfonating the Product of Step (b)

The modified alkylbenzene mixture of step (b) is sulfonated using sulfur trioxide/air. Details of sulfonation using a suitable air/sulfur trioxide mixture are provided in U.S. Pat. No. 3,427,342, Chemithon.

Step (d): Neutralizing the Product of Step (c)

The product of step (c) is neutralized with sodium hydroxide and to give modified alkylbenzene sulfonate, sodium salt mixture.

EXAMPLE 3

Modified Alkylbenzenesulfonate Surfactant Prepared via Vinylidene Olefin Mixture Step (a): Providing Vinylidene Olefin A mixture of 1-pentene, 1-hexene and 1-heptene (1:2:1 mole.) is dimerized at 120° C. by charging it with triethylaluminum (0.02 moles per mole of initial olefins) in a stirred 30-gallon glass-lined Pfaudler reactor. The reactor is heated at autogenous pressure. Reaction time is about 90–100 hours. The reaction is killed with a caustic wash and the organic portion is distilled to remove monomers from the dimers.

Step (b): Alkylating the Product of Step (a) Using an Aromatic Hydrocarbon

To a glass autoclave liner is added 1 mole equivalent of the vinylidene olefin mixture produced in step (a), 20 mole equivalents of benzene and 20 wt. % based on the olefin mixture of a shape selective zeolite catalyst (acidic mordenite catalyst Zeocat™ FM-8/25H). The glass liner is sealed inside a stainless steel rocking autoclave. The autoclave is purged twice with 250 psig $N_2$, and then charged to 1000 psig $N_2$. With mixing, the mixture is heated to 170–190° C. for 14–15 hours at which time it is then cooled and removed from the autoclave. The reaction mixture is filtered to remove catalyst and is concentrated by evaporation of benzene using a rotary evaporator to obtain a clear near-colorless liquid product. The product formed is the desired modified alkylbenzene mixture.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 4

Modified Alkylbenzenesulfonate Surfactant Prepared via Vinylidene Olefin Mixture The procedure of Example 1 is repeated with the exception that the sulfonating step, (c), uses sulfur trioxide (no methylene chloride) as sulfonating agent. Details of sulfonation using a suitable air/sulfur trioxide mixture are provided in U.S. Pat. No. 3,427,342, Chemithon.

EXAMPLE 5

Modified Alkylbenzenesulfonate Surfactant Prepared via Vinylidene Olefin Mixture Step (a): Production of Vinylidene Olefin Mixture 1-hexene is dimerized at 120° C. by charging it with trihexylaluminum (0.02 moles per mole of 1-hexene) in a suitable pressure reactor. The reactor is heated at autogenous pressure. Reaction time is about 90–100 hours. The reaction is killed with a caustic wash and the organic portion is distilled to remove hexenes from the dimers. ($C_{12}$ vinylidene dimer can be obtained in any suitable purity by this method.) See U.S. Pat. Nos. 4,973,788 and 5,569,642 for more detail on the provision of suitable vinylidene olefin. A mixture of 1-pentene and 1-heptene (1:1 molar) is dimerized using a procedure such as the one applied to 1-hexene supra. The products of dimerization are mixed at a ratio of 1:1 molar.

Step (b): Alkylating the Product of Step (a) Using an Aromatic Hydrocarbon

To a glass autoclave liner is added 1 mole equivalent of the mixture of step (a), 20 mole equivalents of benzene and 20 wt. %, based on the olefin mixture, of a shape selective zeolite catalyst (acidic mordenite catalyst Zeocat™ FM-8/25H). The glass liner is sealed inside a stainless steel, rocking autoclave. The autoclave is purged twice with 250 psig $N_2$, and then charged to 1000 psig $N_2$. With mixing, the mixture is heated to 170–190° C. overnight for 14–15 hours at which time it is then cooled and removed from the autoclave. The reaction mixture is filtered to remove catalyst. Benzene is distilled and recycled. A clear colorless or nearly colorless liquid product is obtained.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 6

Modified Alkylbenzenesulfonate Surfactant Prepared via Vinylidene Olefin Mixture The procedure of Example is repeated with the exception that the sulfonating step, (c), uses sulfur trioxide (no methylene chloride) as sulfonating agent. Details of sulfonation using a suitable air/sulfur trioxide mixture are provided in U.S. Pat. No. 3,427,342, Chemithon.

EXAMPLE 7

Cleaning Composition

The procedure of Example 11 is repeated with the exception that the product of step (c) is further treated by the following additional step, (d).

Step (d): Incorporation of the Product of Step (c) into a Cleaning Composition 10% by weight of the product of step (c) is combined with 90% by weight of an agglomerated compact laundry detergent granule.

EXAMPLE 8

Modified Alkylbenzenesulfonate Surfactant Prepared via Vinylidene Olefin Mixture Steps (a) and (b): Internally Isomerizing a Vinylidene Olefin and Concurrently Alkylating it Using an Aromatic Hydrocarbon 2-hexyl-1-decene is obtained from Ethyl Corp. (5022-19-2). To a glass autoclave liner is added 1 mole equivalent of this material, 20 mole equivalents of benzene and 20 wt.%, based on the olefin mixture, of a shape selective zeolite catalyst (acidic mordenite catalyst Zeocat™ FM-8/25H). The glass liner is sealed inside a stainless steel, rocking autoclave. The autoclave is purged twice with 250 psig $N_2$, and then charged to 1000 psig $N_2$. With mixing, the mixture is heated to 150–200° C. for 2–6 hours at which time it is then cooled and removed from the autoclave. The reaction mixture is filtered to remove catalyst. Benzene is distilled and recycled. A clear colorless or nearly colorless liquid product is obtained.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 9

Modified Alkylbenzenesulfonate Surfactant Prepared via Vinylidene Olefin Mixture Step (a): Providing Vinylidene Olefin A mixture of 1-pentene, 1-hexene and 1-heptene is dimerized at 120° C. by charging it with trihexylaluminum (0.02 moles per mole of total alkenes) in a suitable pressure reactor. The reactor is heated at autogenous pressure. Reaction time is about 90–100 hours. The reaction is killed with a caustic wash and the organic portion is distilled to remove parent alkenes from the dimers.

Step (b): Alkylating the Product of Step (a) Using an Aromatic Hydrocarbon

To a glass autoclave liner is added 1 mole equivalent of the vinylidene olefin mixture produced in step (a), 20 mole equivalents of benzene and 20 wt. % based on the olefin mixture of a shape selective zeolite catalyst (acidic mordenite catalyst Zeocat™ FM-8/25H). The glass liner is sealed inside a stainless steel rocking autoclave. The autoclave is purged twice with 250 psig $N_2$, and then charged to 1000 psig $N_2$. With mixing, the mixture is heated to 170–190° C. for 14–15 hours at which time it is then cooled and removed from the autoclave. The reaction mixture is filtered to remove catalyst and is concentrated by evaporation of benzene using a rotary evaporator to obtain a clear near-colorless liquid product. The product formed is the desired modified alkylbenzene mixture.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 10

Cleaning Product Compositions

In this Example, the following abbreviation is used for a modified alkylbenzene sulfonate, sodium salt form or potassium salt form, prepared according to any of the preceding process examples: MAS The following abbreviations are used for cleaning product adjunct materials:

| | |
|---|---|
| Amylase | Amylolytic enzyme, 60 KNU/g, NOVO, Termamyl ® 60T |
| APA | C8–C10 amido propyl dimethyl amine |
| Bicarbonate | Sodium bicarbonate, anhydrous, 400 μm–1200 μm |
| Borax | Na tetraborate decahydrate |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino) stilbene-2:2'-disulfonate |
| C45AS | $C_{14}$–$C_{15}$ linear alkyl sulfate, Na salt |
| CaCl2 | Calcium chloride |
| Carbonate | $Na_2CO_3$ anhydrous, 200 μm–900 μm |
| Cellulase | Cellulolytic enzyme, 1000 CEVU/g, NOVO, Carezyme ® |
| Citrate | Trisodium citrate dihydrate, 86.4%, 425 μm–850 μm |
| Citric Acid | Citric Acid, Anhydrous |
| CMC | Sodium carboxymethyl cellulose |
| CxyAS | $C_{1x}$–$C_{1y}$ alkyl sulfate, Na salt or other salt if specified |
| CxyEz | $C_{1x}$–$C_{1y}$ branched primary alcohol ethoxylate (average z moles of ethylene oxide) |
| CxyEzS | $C_{1x}$–$C_{1y}$ alkyl ethoxylate sulfate, Na salt (average z moles of ethylene oxide; other salt if specified) |
| CxyFA | $C_{1x}$–$C_{1y}$ fatty acid |
| Diamine | Alkyl diamine, e.g., 1,3 propanediamine, Dytek EP, Dytek A, (Dupont) |
| Dimethicone | 40(gum)/60(fluid) wt. blend of SE-76 dimethicone gum (G.E Silicones Div.)/dimethicone fluid of viscosity 350 cS. |
| DTPA | Diethylene triamine pentaacetic acid |
| DTPMP | Diethylene triamine penta (methylene phosphonate), Monsanto (Dequest 2060) |
| Endolase | Endoglucanase, activity 3000 CEVU/g, NOVO |
| EtOH | Ethanol |
| Fatty Acid (C12/14) | C12–C14 fatty acid |
| Fatty Acid (RPS) | Rapeseed fatty acid |
| Fatty Acid (TPK) | Topped palm kernel fatty acid |
| HEDP | 1,1-hydroxyethane diphosphonic acid |
| Isofol 16 | C16 (average) Guerbet alcohols (Condea) |
| LAS | Linear Alkylbenzene Sulfonate (C11.8, Na or K salt) |
| Lipase | Lipolytic enzyme, 100 kLU/g, NOVO, Lipolase ® |
| LMFAA | C12–14 alkyl N-methyl glucamide |
| LMFAA | C12–14 alkyl N-methyl glucamide |
| MA/AA | Copolymer 1:4 maleic/acrylic acid, Na salt, avg. mw. 70,000. |
| $MBAE_x$ | Mid-chain branched primary alkyl ethoxylate (average total carbons = x; average EO = 8) |
| $MBAE_xS_z$ | Mid-chain branched primary alkyl ethoxylate sulfate, Na salt (average total carbons = z; average EO = x) |
| $MBAS_x$ | Mid-chain branched primary alkyl sulfate, Na salt (average total carbons = x) |
| MEA | Monoethanolamine |
| MES | Alkyl methyl ester sulfonate, Na salt |
| MgCl2 | Magnesium chloride |
| MnCAT | Macrocyclic Manganese Bleach Catalyst as in EP 544,440 A or, preferably, use [Mn(Bcyclam)$Cl_2$] wherein Bcyclam = 5,12-dimethyl-1,5,8,12-tetraaza-bicyclo[6.6.2]hexadecane or a comparable bridged tetra-aza macrocycle |
| NaDCC | Sodium dichloroisocyanurate |
| NaOH | Sodium hydroxide |
| NaPS | Paraffin sulfonate, Na salt |
| NaSKS-6 | Crystalline layered silicate of formula δ-$Na_2Si_2O_5$ |
| NaTS | Sodium toluene sulfonate |
| NOBS | Nonanoyloxybenzene sulfonate, sodium salt |
| LOBS | C12 oxybenzenesulfonate, sodium salt |
| PAA | Polyacrylic Acid (mw = 4500) |
| PAE | Ethoxylated tetraethylene pentamine |
| PAEC | Methyl quaternized ethoxylated dihexylene triamine |
| PB1 | Anhydrous sodium perborate bleach of nominal formula $NaBO_2.H_2O_2$ |
| PEG | Polyethylene glycol (mw = 4600) |
| Percarbonate | Sodium Percarbonate, nominal formula $2Na_2CO_3.3H_2O_2$ |
| PG | Propanediol |
| Photobleach | Sulfonated Zinc Phthalocyanine encapsulated in dextrin soluble polymer |
| PIE | Ethoxylated polyethyleneimine |
| Protease | Proteolytic enzyme, 4 KNPU/g, NOVO, Savinase ® |
| QAS | $R_2.N^+(CH_3)_x((C_2H_4O)yH)z$ with $R_2 = C_8$–$C_{18}$ x + z = 3, x = 0 to 3, z = 0 to 3, y = 1 to 15. |
| SAS | Secondary alkyl sulfate, Na salt |
| Silicate | Sodium Silicate, amorphous ($SiO_2$:$Na_2O$; 2.0 ratio) |
| Silicone antifoam | Polydimethylsiloxane foam controller + siloxane-oxyalkylene copolymer as dispersing agent; ratio of foam controller:dispersing agent = 10:1 to 100:1. |

-continued

| | |
|---|---|
| SRP 1 | Sulfobenzoyl end capped esters with oxyethylene oxy and terephthaloyl backbone |
| SRP 2 | Sulfonated ethoxylated terephthalate polymer |
| SRP 3 | Methyl capped ethoxylated terephthalate polymer |
| STPP | Sodium tripolyphosphate, anhydrous |
| Sulfate | Sodium sulfate, anhydrous |
| TAED | Tetraacetylethylenediamine |
| TFA | C16–18 alkyl N-methyl glucamide |
| Zeolite A | Hydrated Sodium Aluminosilicate, $Na_{12}(AlO_2SiO_2)_{12} \cdot 27H_2O$; 0.1–10 $\mu m$ |
| Zeolite MAP | Zeolite (Maximum aluminum P) detergent grade (Crosfield) |

The example is illustrative of the present invention, but is not meant to limit or otherwise define its scope. All parts, percentages and ratios used are expressed as percent weight unless otherwise noted. The following laundry detergent compositions A to E are prepared in accordance with the invention:

| | A | B | C | D | E |
|---|---|---|---|---|---|
| MAS | 22 | 16.5 | 11 | 1–5.5 | 10–25 |
| Any Combination of: | 0 | 1–5.5 | 11 | 16.5 | 0–5 |
| C45 AS | | | | | |
| C45E1S | | | | | |
| LAS | | | | | |
| C16 SAS | | | | | |
| C14–17 NaPS | | | | | |
| C14–18 MES | | | | | |
| MBAS16.5 | | | | | |
| MBAE2S15.5 | | | | | |
| QAS | 0–2 | 0–2 | 0–2 | 0–2 | 0–4 |
| C23E6.5 or C45E7 | 1.5 | 1.5 | 1.5 | 1.5 | 0–4 |
| Zeolite A | 27.8 | 0 | 27.8 | 27.8 | 20–30 |
| Zeolite MAP | 0 | 27.8 | 0 | 0 | 0 |
| PAA | 2.3 | 2.3 | 2.3 | 2.3 | 0–5 |
| Carbonate | 27.3 | 27.3 | 27.3 | 27.3 | 20–30 |
| Silicate | 0.6 | 0.6 | 0.6 | 0.6 | 0–2 |
| PB1 | 1.0 | 1.0 | 0–10 | 0–10 | 0–10 |
| NOBS | 0–1 | 0–1 | 0–1 | 0.1 | 0.5–3 |
| LOBS | 0 | 0 | 0–3 | 0 | 0 |
| TAED | 0 | 0 | 0 | 2 | 0 |
| MnCAT | 0 | 0 | 0 | 0 | 2 ppm |
| Protease | 0–0.5 | 0–0.5 | 0–0.5 | 0–0.5 | 0–0.5 |
| Cellulase | 0–0.3 | 0–0.3 | 0–0.3 | 0–0.3 | 0–0.5 |
| Amylase | 0–0.5 | 0–0.5 | 0–0.5 | 0–0.5 | 0–1 |
| SRP 1 or SRP 2 | 0.4 | 0.4 | 0.4 | 0.4 | 0–1 |
| Brightener 1 or 2 | 0.2 | 0.2 | 0.2 | 0.2 | 0–0.3 |
| PEG | 1.6 | 1.6 | 1.6 | 1.6 | 0–2 |
| Silicone Antifoam | 0.42 | 0.42 | 0.42 | 0.42 | 0–0.5 |
| Sulfate, Moisture & Minors | ---Balance--- | | | | |
| Density (g/L) | 663 | 663 | 663 | 663 | 600–700 |

EXAMPLE 11

Cleaning Product Compositions

The following liquid laundry detergent compositions F to J are prepared in accord with the invention. Abbreviations are as used in the preceding Examples.

| | F | G | H | I | J |
|---|---|---|---|---|---|
| MAS | 1–7 | 7–12 | 12–17 | 17–22 | 1–35 |
| Any combination of: C25 AExS*Na | 15–21 | 10–15 | 5–10 | 0–5 | 0–25 |

-continued

| | F | G | H | I | J |
|---|---|---|---|---|---|
| MAS | 1–7 | 7–12 | 12–17 | 17–22 | 1–35 |
| (x = 1.8 – 2.5) | | | | | |
| MBAE1.8S15.5 | | | | | |
| MBAS15.5 | | | | | |
| C25 AS (linear to high 2-alkyl) | | | | | |
| C 14–17 NaPS | | | | | |
| C 12–16 SAS | | | | | |
| C 18 1,4 disulfate | | | | | |
| LAS | | | | | |
| C 12–16 MES | | | | | |
| LMFAA | 0–3.5 | 0–3.5 | 0–3.5 | 0–3.5 | 0–8 |
| C23E9 or C23E6.5 | 0–2 | 0–2 | 0–2 | 0–2 | 0–8 |
| APA | 0–0.5 | 0–0.5 | 0–0.5 | 0–0.5 | 0–2 |
| Citric Acid | 5 | 5 | 5 | 5 | 0–8 |
| Fatty Acid (TPK or C12/14) | 2 | 2 | 2 | 2 | 0–14 |
| EtOH | 4 | 4 | 4 | 4 | 0–8 |
| PG | 6 | 6 | 6 | 6 | 0–10 |
| MEA | 1 | 1 | 1 | 1 | 0–3 |
| NaOH | 3 | 3 | 3 | 3 | 0–7 |
| Na TS | 2.3 | 2.3 | 2.3 | 2.3 | 0–4 |
| Na formate | 0.1 | 0.1 | 0.1 | 0.1 | 0–1 |
| Borax | 2.5 | 2.5 | 2.5 | 2.5 | 0–5 |
| Protease | 0.9 | 0.9 | 0.9 | 0.9 | 0–1.3 |
| Lipase | 0.06 | 0.06 | 0.06 | 0.06 | 0–0.3 |
| Amylase | 0.15 | 0.15 | 0.15 | 0.15 | 0–0.4 |
| Cellulase | 0.05 | 0.05 | 0.05 | 0.05 | 0–0.2 |
| PAE | 0–0.6 | 0–0.6 | 0–0.6 | 0–0.6 | 0–2.5 |
| PIE | 1.2 | 1.2 | 1.2 | 1.2 | 0–2.5 |
| PAEC | 0–0.4 | 0–0.4 | 0–0.4 | 0–0.4 | 0–2 |
| SRP 2 | 0.2 | 0.2 | 0.2 | 0.2 | 0–0.5 |
| Brightener 1 or 2 | 0.15 | 0.15 | 0.15 | 0.15 | 0–0.5 |
| Silicone antifoam | 0.12 | 0.12 | 0.12 | 0.12 | 0–0.3 |
| Fumed Silica | 0.0015 | 0.0015 | 0.0015 | 0.0015 | 0–0.003 |
| Perfume | 0.3 | 0.3 | 0.3 | 0.3 | 0–0.6 |
| Dye | 0.0013 | 0.0013 | 0.0013 | 0.0013 | 0–0.003 |
| Moisture/minors | Balance | Balance | Balance | Balance | Balance |
| Product pH (10% in DI water) | 7.7 | 7.7 | 7.7 | 7.7 | 6–9.5 |

What is claimed is:

1. A cleaning product comprising:
   (i) from about 0.1% to about 99% of a modified alkylarylsulfonate surfactant, wherein said modified alkylarylsulfonate surfactant is the product of a process comprising the following steps:
   (a) a step of reacting, in the presence of a dimerization catalyst, an olefinic feedstock comprising alpha-olefins or mixtures thereof to form one or more vinylidene olefins having a carbon content of from $C_{10}$ to $C_{16}$;

(b) a step of alkylating an arene selected from benzene, toluene and mixtures thereof, with said vinylidene olefin, in the presence of an alkylation catalyst;

(c) a step of sulfonating the product of step (b); and, optionally, (d) a step of neutralizing the product of step (c); and (ii) from about 0.00001% to about 99% of cleaning product adjuncts.

2. A cleaning product according to claim 1 wherein said modified alkylarylsulfonate surfactant is the modified alkylbenzenesulfonate surfactant formed when said arene is benzene; and wherein said cleaning product composition comprises:

(i) from about 1% to about 40% of said modified alkylarenesulfonate surfactant; and (ii) from about 0.01% to about 99% of said cleaning product adjuncts and wherein said cleaning product adjuncts are adjuncts suitable for laundry detergents and comprise at least one member selected from the group consisting of detersive enzymes, oxygen bleaches, bleach activators, bleach catalysts, photobleaches, brighteners, detersive adjunct polymers, surfactants other than said modified alkylarylsulfonate surfactant, and mixtures thereof.

3. A cleaning product according to claim 2 wherein said alkylation step has an internal isomer selectivity of from 0 to no more than about 40.

4. A cleaning product according to claim 3 wherein $C_{11}$–$C_{14}$ alkyl carbon content of said modified alkylbenzenesulfonate surfactant is increased relative to the alkyl carbon content which would be obtained by indiscriminate reaction of said feedstock olefins having varying chain-lengths in said step (a); and wherein said increase in $C_{11}$–$C_{14}$ alkyl carbon content is achieved in step (a) by means of any one of:

(I) selecting the feedstock wherein the alpha-olefins consist essentially of a ternary mixture of $C_5$+$C_6$+$C_7$ alpha olefins;

(II) selecting the feedstock wherein the alpha-olefins consist essentially of a binary mixture selected from a mixture of $C_5$+$C_7$ alpha-olefins and a mixture of $C_6$+$C_7$ alpha olefins; and (III) selecting the feedstock wherein the alpha-olefins consist essentially of a single alpha-olefin having carbon content of $C_6$ or $C_7$;

thereby minimizing formation of vinylidene olefins having carbon content of either less than or equal to $C_{10}$ or of greater than or equal to $C_{15}$.

5. A cleaning product according to claim 2 wherein said cleaning product adjuncts further comprise a builder other than a polymeric builder.

6. A cleaning product according to claim 5 wherein said builder is a zeolite builder.

7. A cleaning product according to claim 6 wherein said zeolite builder is selected from the group consisting of zeolite A, zeolite P, zeolite maximum aluminum P and mixtures thereof.

8. A cleaning product according to claim 2 wherein said cleaning product adjuncts comprise at least one detersive enzyme selected from the group consisting of proteases, amylases, lipases, cellulases, keratinases, endoglucanases, and mixtures thereof.

9. A cleaning product according to claim 8 wherein said detersive enzyme comprises at least one of said detersive enzymes other than protease.

10. A cleaning product according to claim 2 wherein said surfactant other than said modified alkylarylsulfonate surfactant comprises a linear alkylbenzenesulfonate surfactant; or wherein prior to step (c), the product of step (b) is blended with a linear alkylbenzene; or wherein prior to or concurrent with step (d), the product of step (c) is blended with a linear alkylbenzenesulfonic acid.

11. A cleaning product according to claim 10 wherein said modified alkylbenzenesulfonate surfactant and said linear alkylbenzenesulfonate surfactant are present at a ratio of from 1:100 to 100:1.

12. A cleaning product according to claim 2 wherein said modified alkylbenzenesulfonate surfactant is the product of the process wherein said step (a) of reacting said feedstock to form said vinylidene olefin is followed by an additional step, prior to said step (b), of separating vinylidene olefin from deep internal olefins and/or oligomers suitable for lubricant oil manufacture.

13. A cleaning product according to claim 2 wherein said modified alkylbenzenesulfonate surfactant is the product of the process wherein said step (a) of reacting said alpha-olefin to form said vinylidene olefin comprises dimerizing, in presence of a dimerization catalyst, a substantially linear alpha-olefin having about half the molecular weight required to form a C10–C14 vinylidene olefin, thereby forming a vinylidene olefin under high-yield conditions not requiring separation of the vinylidene olefin from oligomers or deep internal isomers.

14. A cleaning product according to claim 2 wherein said dimerization catalyst in step (a) is an aluminum alkyl and wherein step (a) comprises dimerizing said alpha-olefin at a temperature of 165°±3° C. with a reaction period in the range of from about 6 hours to about 12 hours sufficient to convert at least 85% by weight of said alpha-olefin to a vinylidene olefin-rich product with at least 80 wt % vinylidene dimer selectivity.

15. A cleaning product according to claim 2 wherein said dimerization catalyst in step (a) is an aluminum alkyl and wherein step (a) comprises dimerizing said alpha-olefin using from 0.001–0.04 moles of said catalyst per mole of said alpha-olefin at a temperature in the range of about 100° to about 140° C. for a time sufficient to convert at least 80 mole percent of the initial alpha-olefin to a vinylidene olefin-rich product with at least 80 wt % vinylidene dimer selectivity.

16. A cleaning product according to claim 2 wherein said dimerization catalyst in said step (a) is an aluminum alkyl and wherein step (a) comprises dimerizing said alpha-olefin using from 0.001–0.04 moles of said catalyst per mole of said alpha-olefin; and further wherein said step (a) is conducted using measures to limit reactor wall reactions and/or loss of catalyst.

17. A cleaning product according to claim 2 wherein in said step (a), oligomerization and/or deep internal olefin production are minimized by control of reaction temperature and time.

18. A cleaning product according to claim 2 wherein the vinylidene olefin containing product of said step (a) is reacted in step (b) without prior separation or extraction of oligomeric byproducts.

19. A cleaning product according to claim 2 wherein said dimerization catalyst in said step (a) is selected from trialkylaluminum catalysts and metallocene catalysts.

20. A cleaning product according to claim 2 wherein said cleaning product adjuncts are adjuncts other than those used in lube oil additives and/or enhanced oil recovery.

21. A process comprising:

(a) a dimerization step, comprising reacting, in the presence of a dimerization catalyst, an olefinic feedstock comprising alpha-olefins or mixtures thereof to form one or more vinylidene olefins having a carbon content of from $C_{10}$ to $C_{16}$; and (b) an alkylation step having an internal isomer selectivity of from 1 to 40, comprising reacting in the presence of an alkylation catalyst, an arene selected from benzene, toluene and mixtures thereof, with said vinylidene olefin;

whereby a modified alkylarene is produced, said modified alkylarene being useful as a precursor for alkylarylsulfonate surfactants adapted for use in cleaning products.

22. A process according to claim 21 wherein said arene is benzene; said process further comprising:

(c) a sulfonation step, comprising reacting the product of step (b) with a sulfonating agent;

whereby a modified alkylbenzenesulfonic acid is produced, said modified alkylbenzenesulfonic acid being adapted for use in cleaning products.

23. A process according to claim 22, further comprising:

(d) a neutralization step, comprising reacting the product of step (c) with an alkali;

whereby a modified alkylbenzenesulfonate surfactant is produced, said modified alkylbenzenesulfonate surfactant being adapted for use in cleaning products.

24. A process according to claim 23 wherein said internal isomer selectivity of step (b) is no more than about 20.

25. A process according to claim 24 wherein in said step (a), said dimerization catalyst is selected from alkylaluminum catalysts and metallocene catalysts.

26. A process according to claim 25 wherein said alkylation catalyst in step (b) is selected from shape-selective zeolite-containing alkylation catalysts in at least partially acidic form.

27. A process according to claim 26 wherein said zeolite in step (b) is selected from the group consisting of mordenite, ZSM-4, ZSM-12, ZSM-20, offretite, gmelinite and zeolite beta in at least partially acidic form.

28. A process according to claim 27 wherein said internal isomer selectivity in step (b) is from 0 to 10 and wherein said alkylation catalyst in step (b) is substantially in acid form and is contained in a catalyst pellet comprising a conventional binder and further, wherein said catalyst pellet comprises at least about 5% of said alkylation catalyst.

29. A process according to claim 27 wherein in said step (b), said alkylation catalyst is selected from at least partially acidic mordenite, at least partially acidic, at least partially dealuminized mordenite; and at least partially acidic zeolite beta.

30. A process according to claim 29 wherein said alkylation catalyst in step (b) consists essentially of dealuminized H-mordenite.

31. A process according to claim 21 wherein aluminum chloride is substantially absent in step (b).

32. A process according to claim 21 wherein HF is substantially absent in step (b).

33. A process according to claim 21 wherein fluoridated zeolites are substantially absent in step (b).

34. A process according to claim 21 wherein sulfuric acid is substantially absent in step (b).

35. A process according to claim 21 wherein free mineral acids are substantially absent in step (b).

36. A process according to claim 21 wherein Lewis acids in soluble form are substantially absent in step (b).

37. A process according to claim 21, wherein $C_{11}$–$C_{14}$ alkyl carbon content of said modified alkylbenzenesulfonate surfactant is increased relative to the alkyl carbon content which would be obtained by indiscriminate reaction of said feedstock olefins having varying chainlengths in said step (a); wherein said increase in $C_{11}$–$C_{14}$ alkyl carbon content is achieved in said step (a) by means of any one of:

(I) selecting the feedstock wherein the alpha-olefins consist essentially of a ternary mixture of $C_5+C_6+C_7$ alpha olefins;

(II) selecting the feedstock wherein the alpha-olefins consist essentially of a binary mixture selected from a mixture of $C_5+C_7$ alpha-olefins and a mixture of $C_6+C_7$ alpha olefins; and (III) selecting the feedstock wherein the alpha-olefins consist essentially of a single alpha-olefin having carbon content of $C_6$ or $C_7$;

thereby minimizing formation of vinylidene olefins having carbon content of either less than or equal to $C_{10}$ or of greater than or equal to $C_{15}$.

38. A process according to claim 21 wherein said step (a) is conducted subject to at least one of:

I. minimizing oligomerization and/or deep internal olefin production by control of temperature and time; and II. conducting said step (a) without separation or extraction of said vinylidene olefin from oligomers.

39. A process according to claim 22 wherein in said sulfonation step, (c), said sulfonating agent is selected from sulfur trioxide, oleum, chlorosulfonic acid, and sulfuric acid.

40. A process according to claim 39 wherein in said sulfonation step, (c), said sulfonating agent is other than chlorosulfonic acid.

41. A process according to claim 23 wherein in said neutralization step, (d), said alkali is selected from sodium, potassium, ammonium, magnesium and substituted ammonium alkalis and mixtures thereof.

42. A process according to claim 41 wherein said alkali is selected from sodium hydroxide, potassium hydroxide, ammonium hydroxide, sodium carbonate, potassium carbonate, and mixtures thereof.

43. A process according to claim 23, further comprising:

(e) a step of combining the product of step (d) with a cleaning product adjunct;

whereby a cleaning product composition is produced.

44. A method for improving a domestic cleaning product containing alkylarylsulfonate surfactant comprising (I) at least one stage of introducing light branching into a linear alkylarene by at least one step of dimerizing an alpha-olefin to form a vinylidene olefin and at least one step of alkylating the vinylidene olefin using an alkylation catalyst having internal isomer selectivity of from 0 to no more than about 40;

(II) at least one step of sulfonating the lightly branched modified alkylarene of stage (I); and (III) at least one step of formulating the resulting lightly branched alkylarylsulfonate surfactant, in acid or salt form, and at least one adjunct, into said domestic cleaning product composition.

* * * * *